United States Patent
Panyam et al.

(10) Patent No.: US 10,166,304 B2
(45) Date of Patent: Jan. 1, 2019

(54) ANTIBODY FRAGMENTS FOR DETECTING CANCER AND METHODS OF USE

(71) Applicant: REGENTS OF THE UNIVERSITY OF MINNESOTA, Minneapolis, MN (US)

(72) Inventors: Jayanth Panyam, Minneapolis, MN (US); Stephen Kalscheuer, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/325,696

(22) PCT Filed: Jul. 10, 2015

(86) PCT No.: PCT/US2015/040044
§ 371 (c)(1),
(2) Date: Jan. 11, 2017

(87) PCT Pub. No.: WO2016/007919
PCT Pub. Date: Jan. 14, 2016

(65) Prior Publication Data
US 2017/0157275 A1 Jun. 8, 2017

Related U.S. Application Data

(60) Provisional application No. 62/023,354, filed on Jul. 11, 2014.

(51) Int. Cl.
| | | |
|---|---|---|
| *C07K 16/00* | (2006.01) | |
| *A61K 51/10* | (2006.01) | |
| *A61K 49/00* | (2006.01) | |
| *C07K 16/30* | (2006.01) | |
| *G01N 33/574* | (2006.01) | |
| *G01N 33/68* | (2006.01) | |
| *A61K 47/68* | (2017.01) | |
| *A61K 47/69* | (2017.01) | |

(52) U.S. Cl.
CPC ...... *A61K 51/1066* (2013.01); *A61K 47/6855* (2017.08); *A61K 47/6865* (2017.08); *A61K 47/6869* (2017.08); *A61K 47/6929* (2017.08); *A61K 49/0039* (2013.01); *A61K 49/0093* (2013.01); *A61K 51/1027* (2013.01); *A61K 51/1051* (2013.01); *C07K 16/30* (2013.01); *G01N 33/5743* (2013.01); *G01N 33/57415* (2013.01); *G01N 33/57434* (2013.01); *G01N 33/6857* (2013.01); *C07K 2317/21* (2013.01); *C07K 2317/622* (2013.01); *C07K 2317/626* (2013.01); *C07K 2317/77* (2013.01); *C07K 2319/30* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Albert et al. | |
| 4,816,567 A | 3/1989 | Cabilly et al. | |
| 4,873,192 A | 10/1989 | Kunkel | |
| 4,946,778 A | 8/1990 | Ladner et al. | |
| 5,091,513 A | 2/1992 | Huston et al. | |
| 5,260,203 A | 11/1993 | Ladner et al. | |
| 5,455,030 A | 10/1995 | Ladner et al. | |
| 6,432,636 B1 * | 8/2002 | Maresh | C07K 14/4711 435/6.16 |
| 8,501,418 B2 * | 8/2013 | Kas | G01N 33/6893 435/7.1 |
| 2008/0248050 A1 | 10/2008 | Stevens | |
| 2010/0008937 A1 * | 1/2010 | Peer | C12N 15/111 514/1.1 |
| 2012/0034240 A1 | 2/2012 | Kas et al. | |

FOREIGN PATENT DOCUMENTS

| | | |
|---|---|---|
| EP | 0058481 A1 | 8/1982 |
| EP | 0133988 A2 | 3/1985 |
| EP | 0239400 A2 | 9/1987 |
| EP | 0404097 A2 | 12/1990 |
| WO | 1993011161 A1 | 6/1993 |
| WO | 1996002576 A1 | 2/1996 |
| WO | 2013040188 A1 | 3/2013 |

OTHER PUBLICATIONS

CN102936598 B (Apr. 16, 2014) english translation.*
Adams et al (British Journal of Cancer, 1998, 77(9): 1405-1412).*
Burgess et al. (J. Cell Biol. 111:2129-2138, 1990).*
Lazar et al. ( Mol. Cell Biol. 8:1247-1252, 1998).*
Aktas, et al., "Stem cell and epithelial-mesenchymal transition markers are frequently overexpressed in circulating tumor cells of metastatic breast cancer patients", Breast Cancer Res. 11(4), R46 (2009).
Altschul, et al., "Basic local alignment search tool", J Mol Biol 215, 403-410 (1990).
Altschul, et al., "Gapped BLAST and PSI-BLAST: a new generation of protein database search programs", Nucleic Acids Res 25 (17), 3389-3402 (1997).
American Cancer Society, Cancer Facts & Figures, 72 pages (2014).
Anderl, et al., "Antibody-drug conjugate payloads", Methods Mol Biol. 1045, 51-70 (2013).
Batzer, et al., "Enhanced evolutionary PCR using oligonucleotides with inosine at the 3'-terminus", Nucl. Acids Res. 19(18), 5081 (1991).
Behrens, et al., "Methods for site-specific drug conjugation to antibodies", MAbs. 6(1), 46-53 (2014).

(Continued)

*Primary Examiner* — Sean E Aeder
(74) *Attorney, Agent, or Firm* — Viksnins Harris Padys Malen LLP

(57) ABSTRACT

The present invention relates to diagnostic and therapeutic agents comprising recombinant antibody fragments to bind a protein associated with cancer and methods of use of these diagnostic and therapeutic agents.

24 Claims, 17 Drawing Sheets

Specification includes a Sequence Listing.

(56) References Cited

OTHER PUBLICATIONS

Better, et al., "Expression of engineered antibodies and antibody fragments in microorganisms", Methods in Enzymology 178, 476-496 (1989).
Bird, et al., "Single Chain Antibody Variable Regions", Tibtech 9, 132-137 (1991).
Bonnomet, et al., "Epithelial-to-mesenchymal transitions and circulating tumor cells", J Mammary Gland Biol Neoplasia. 15(2), 261-273 (2010).
Brabletz, et al., "Migrating cancer stem cells—an integrated concept of malignant tumour progression", Nat Rev Cancer. 5(9), 744-749 (2005).
Brennan, et al., "Preparation of Bispecific Antibodies by Chemical Recombination of Monoclonal Immunoglobulin G1 Fragments", Science 229, 81-83 (1985).
Carter, et al., "High Level *Escherichia coli* Expression and Production of a Bivalent Humanized Antibody Fragment", Bio/Technology 10, 163-167 (1992).
Christianson, et al., "ScFv anti-heparan sulfate antibodies unexpectedly activate endothelial and cancer cells through p38 MAPK: implications for antibody-based targeting of heparan sulfate proteoglycans in cancer", PLoS One 7 (11), e49092, 12 pages (2012).
Clackson, et al., "Making antibody fragments using phage display libraries", Nature 352, 624-628 (1991).
Co, et al., "A humanized antibody specific for the platelet integrin gpIIb/IIIa", J Immunol 152, 2968-2976 (1994).
Corpet, "Multiple sequence alignment with hierarchical clustering", Nucl Acids Res 16, 10881-10890 (1988).
Dalbadie-McFarland, et al., "Oligonucleotide-directed mutagenesis as a general and powerful method for studies of protein function", Proc Natl Acad Sci. 79(21), 6409-6413 (1982).
Dean, et al., "Tumour stem cells and drug resistance", Nat Rev Cancer. 5(4), 275-284 (2005).
Ducry, "Antibody-Drug Conjugates", Methods in Molecular Biology, vol. 1045, 51-70 (2013).
Higgins, et al., "CLUSTAL: a package for performing multiple sequence alignment on a microcomputer", Gene 73, 237-244 (1988).
Higgins, et al., "Fast and sensitive multiple sequence alignments on a microcomputer", CABIOS 5(2), 151-153 (1989).
Holliger, et al., ""Diabodies": Small bivalent and bispecific antibody fragments", Proc. Natl. Acad. Sci. 90, 6444-6448 (1993).
Huang, et al., "Parallelization of a local similarity algorithm", CABIOS 8, 155-165 (1992).
Huston, et al., "Protein engineering of antibody binding sites: Recovery of specific activity in an anti-digoxin single-chain Fv analogue produced in *Escherichia coli*", Proc. Natl. Acad. Sci. 85, 5879-5883 (1988).
Jones, et al., "Replacing the complementarity-determining regions in a human antibody with those from a mouse", Nature 321, 522-525 (1986).
Kallergi, et al., "Epithelial to mesenchymal transition markers expressed in circulating tumour cells of early and metastatic breast cancer patients", Breast Cancer Res. 13(3), R59 (2011).
Kalluri, et al., "Fibroblasts in cancer", Nat Rev Cancer. 6(5), 392-401 (2006).
Karlin, et al. "Applications and statistics for multiple high-scoring segments in molecular sequences", Proc Natl Acad Sci 90, 5873-5877 (1993).
Karlin, et al., "Methods for assessing the statistical significance of molecular sequence features by using general scoring schemes", Proc Natl Acad Sci 87(6), 2264-2268 (1990).
Kohler, et al., "Continuous cultures of fused cells secreting antibody of predefined specificity", Nature 256, 495-497 (1975).
Kunkel, "Rapid and efficient site specific mutagenesis without phenotypic selection", Proc. Natl Acad Sci vol. 82, 488-492 (1985).
Kunkel, et al., "Rapid and Efficient Site-Specific Mutagenesis without Phenotypic Selection", Methods in Enzymology vol. 154, 367-382 (1987).
Lamoyi, "Preparation of F(ab')2 fragments from mouse IgG of various subclasses", Methods Enzymol 121, 652-663 (1986).
Langer, et al., "Biocompatibility of polymeric delivery systems for macromolecules", J. Biomed. Mater. Res. 15, 267-277 (1981).
Langer, "Controlled release of macromolecules", Chem. Tech. 12, 98-105 (1982).
Malhotra, et al., "Histological, molecular and functional subtypes of breast cancers", Cancer Biol Ther. 10(10), 955-60 (2010).
Mark, et al. "Site-specific mutagenesis of the human fibroblast interferon gene", Proc Natl Acad Sci. 81(18), 5662-5666 (1984).
Marks, et al., "By-passing Immunization, Human Antibodies from V-Gene Libraries Displayed on Phage", J. Mol. Biol. 222, 581-597 (1991).
Marks, et al., "By-Passing Immunization: Building High Affinity Human Antibodies by Chain Shuffling", Bio/Technology 10, 779-783 (1992).
McCafferty, et al., "Phage antibodies: filamentous phage displaying antibody variable domains", Nature 348, 552-554 (1990).
Meinkoth, et al., "Hybridization of nucleic acids immobilized on solid supports", Anal Biochem.138(2), 267-284 (1984).
Millner, et al., "Circulating tumor cells: a review of present methods and the need to identify heterogeneous phenotypes", Ann Clin Lab Sci. 43(3), 295-304 (2013).
Morimoto, et al., "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods 24, 107-117 (1992).
Morrison, et al., "Chimeric human antibody molecules: Mouse antigen-binding domains with human constant region domains", Proc. Natl. Acad. Sci. USA 8I, 6851-6855 (1984).
Murdoch, et al., "Widespread Expression of Perlecan Proteoglycan in Basement Membranes adn Extracellular Matrices of Human Tissues as Detected by a Novel Monoclonal Antibody Against Domain III and by In Situ Hybridization", Journal of Histochemistry and Cytochemistry 42(2), 239-249 (1994).
Myers, et al., "Optimal alignments in linear space", CABIOS 4 (1), 11-7 (1988).
Needleman, et al., "A general method applicable to the search for similarities in teh amino acid sequence of two proteins", J. Mol. Biol. 48, 443-453 (1970).
Ohtsuka, et al., "An Alternative Approach to Deoxyoligonucleotides as Hybridization Probes by Insertion of Deoxyinosine at Ambiguous Codon Positions", Journal of Biological Chemistry 260(5), 2605-2608 (1985).
Pantel, et al., "Detection and clinical implications of early systemic tumor cell dissemination in breast cancer", Clin Cancer Res. 9(17), 6326-6334 (2003).
Patani, et al., "Clinical significance of sentinel lymph node isolated tumour cells in breast cancer", Breast Cancer Res Treat. 127(2), 325-334 (2011).
Patent Cooperation Treaty, International Search Report and Written Opinion for PCT/US2015/40044, 12 pages, dated Jan. 6, 2016.
Pearson, et al., "Improved tools for biological sequence comparison", Proc Natl Acad Sci 85, 2444-2448 (1988).
Pearson, "Using the FASTA program to search protein and DNA sequence databases", Meth. Mol. Biol. 24, 307-331 (1994).
Presta, "Antibody engineering", Curr. Op. Struct. Biol. vol. 2, 593-596 (1992).
Reichmann, et al., "Reshaping human antibodies for therapy", Nature 332(6162), 323-327 (1988).
Rosenburg, et al., "The Pharmacology of Monoclonal Antibodies. Chapter 11 Antibodies from *Escherichia coli*", Springer Verlag, NY., Chapter 11, vol. 113, 269-315 (1994).
Rossolini, et al., "Use of deoxyinosine-containing primers vs degenerate primers for polymerase chain reaction based on ambiguous sequence information", Mol. Cell. Probes 8, 91 (1994).
Sato, et al., "Reshaping a Human Antibody to Inhibit the Interleukin 6-dependent Tumor Cell Growth", Cancer Res. 53, 851-856 (1993).
Sidman, et al., "Controlled Release of Macromolecules and Pharmaceuticals from Synthetic Polypeptides Based on Glutamic Acid", Biopolymers 22, 547-556 (1983).

(56) References Cited

OTHER PUBLICATIONS

Smith, et al., "Comparison of biosequences", Adv. Appl. Math. 2(4), 482-489 (1981).

Trumpp, et al., "Mechanisms of Disease: cancer stem cells—targeting the evil twin", Nat Clin Pract Oncol. 5(6), 337-347 (2008).

Tsuji, et al., "Epithelial-mesenchymal transition induced by growth suppressor p12CDK2-AP1 promotes tumor cell local invasion but suppresses distant colony growth", Cancer Res. 68(24), 10377-10386 (2008).

Turner, et al., "The potential exploitation of plant viral translational enhancers in biotechnology for increased gene expression", Mol. Biotech. 3(3), 225-236 (1995).

Wang, et al. "Site-specific mutagenesis of the human interleukin-2 gene: structure-function analysis of the cysteine residues", Science 224(4656), 1431-1433 (1984).

Waterhouse, et al., "Combinatoial infection and in vivo recombination: a strategy for making large phage antibody repertoires", Nucleic Acids Res. 21 (9), 2265-2266 (1993).

Xu, et al., "Gene transcriptional networks integrate microenvironmental signals in human breast cancer", Integr Biol. 3 (4), 368-374 (2011).

Yang, et al., "Exploring a new twist on tumor metastasis", Cancer Res. 66(9), 4549-4552 (2006).

Zoller, et al., "Oligonucleotide-directed mutagenesis using M13-derived vectors: an efficient and general procedure for the production of point mutations in any fragment of DNA", Nucleic Acids Res. 10(20), 6487-6500 (1982).

\* cited by examiner

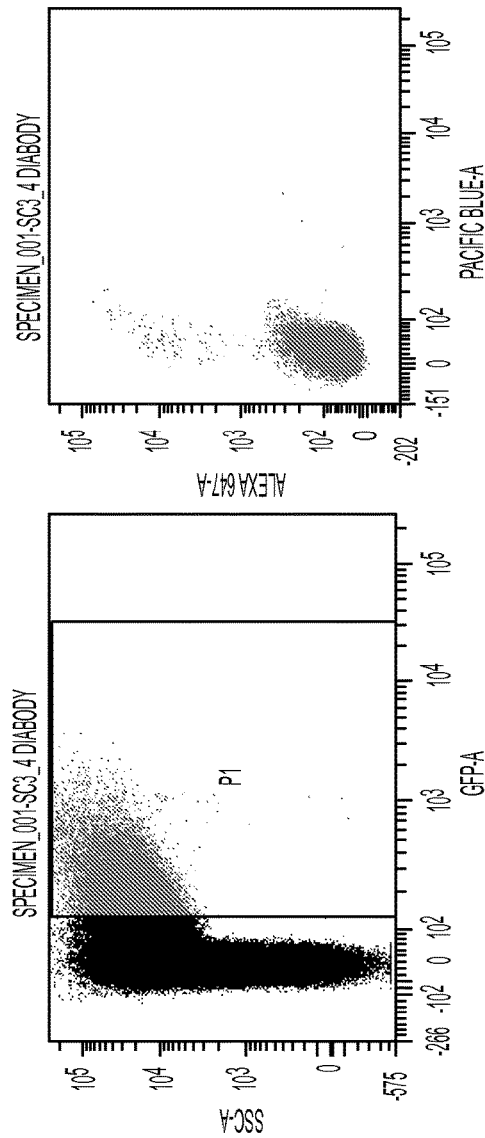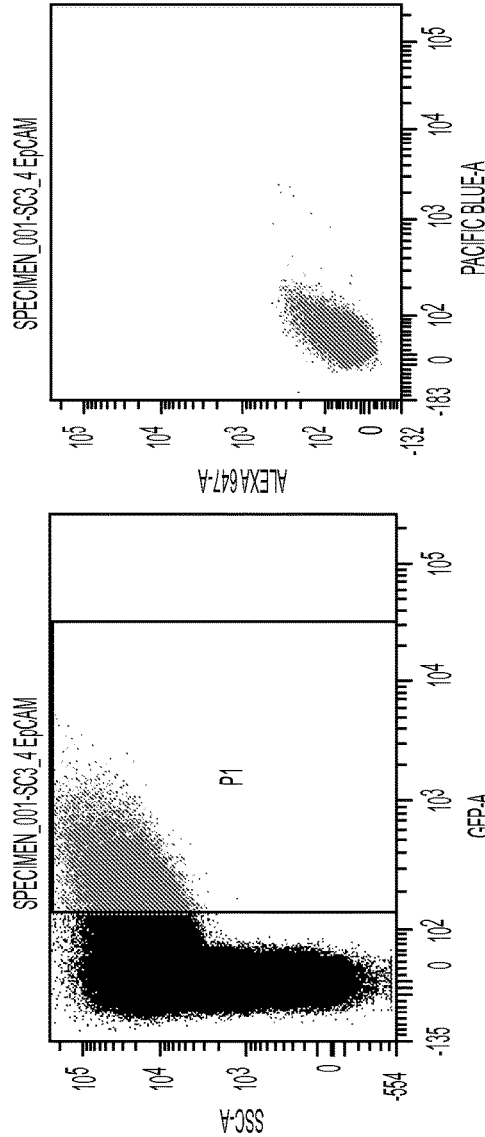
FIG. 6C
FIG. 6D

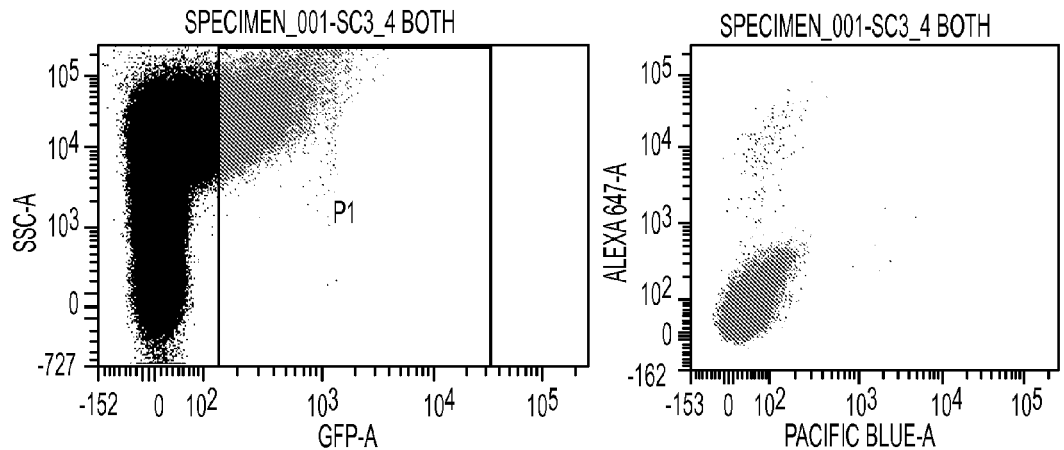

FIG. 6E

Tw1_S4 Clone #6 sequence

DNA sequence

AAGGAGACAGTCATAATGAAATACCTATTGCCTACGGCAGCCGCTGGATTGTTATTACTC
GCGGCCCAGCCGGCCATGGCCGAGGTGCAGCTGTTGGAGTCTGGGGGAGGCTTGGTACAG
CCTGGGGGGTCCCTGAGACTCTCCTGTGCAGCCTCTGGATTCACCTTTAGCAGCTATGCC
ATGAGCTGGGTCCGCCAGGCTCCAGGGAAGGGGCTGGAGTGGGTCTCAGCGATTAGGGAG
GATGGTATTAAGACATATTACGCAGACTCCGTGAAGGGCCGGTTCACCATCTCCAGAGAC
AATTCCAAGAACACGCTGTATCTGCAAATGAACAGCCTGAGAGCCGAGGACACGGCCGTA
TATTACTGTGCGAAAAGGGCTCGTCGGTTTGACTACTGGGGCCAGGGAACCCTGGTCACC
GTCTCGAGCGGTGGAGGCGGTTCAGGCGGAGGTGGCAGCGGCGGTGGCGGGTCGACGGAC
ATCCAGATGACCCAGTCTCCATCCTCCCTGTCTGCATCTGTAGGAGACAGAGTCACCATC
ACTTGCCGGGCAAGTCAGAGCATTAGCAGCTATTTAAATTGGTATCAGCAGAAACCAGGG
AAAGCCCCTAAGCTCCTGATCTATAATGCATCCCTTTTGCAAAGTGGGGTCCCATCAAGG
TTCAGTGGCAGTGGATCTGGGACAGATTTCACTCTCACCATCAGCAGTCTGCAACCTGAA
GATTTTGCAACTTACTACTGTCAACAGAGTCTGCGTTCGCCTATTACGTTCGGCCAAGGG
ACCAAGGTGGAAATCAAACGGGCGGCCGCACATCATCATCACCATCAC(SEQ ID NO:1)

Protein sequence

MKYLLPTAAAGLLLLAAQPAMAEVQLLESGGGLVQPGGSLRLSCAASGFTFSSYAMSWVR
QAPGKGLEWVSAIREDGIKTYYADSVKGRFTISRDNSKNTLYLQMNSLRAEDTAVYYCAK
RARRFDYWGQGTLVTVSSGGGGSGGGGSGGGGSTDIQMTQSPSSLSASVGDRVTITCRAS
QSISSYLNWYQQKPGKAPKLLIYNASLLQSGVPSRFSGSGSGTDFTLTISSLQPEDFATY
YCQQSLRSPITFGQGTKVEIKRAAAHHHHHH(SEQ ID NO:2)

FIG. 7

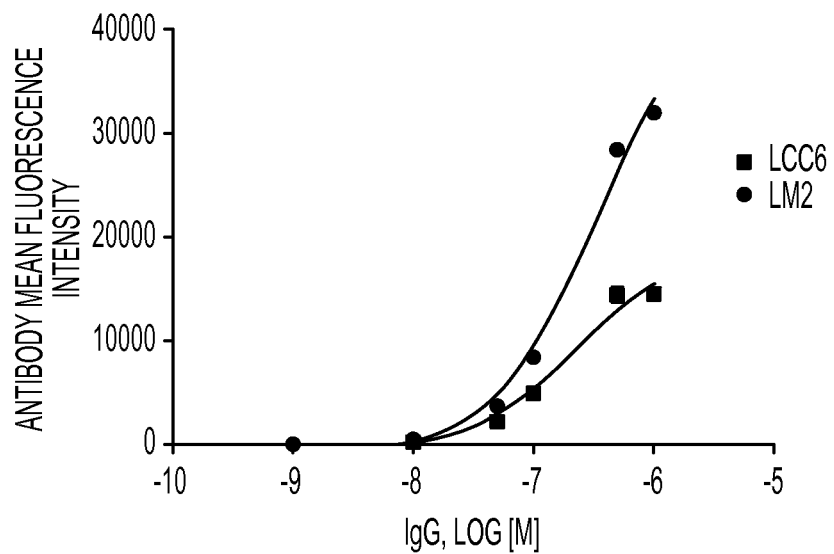
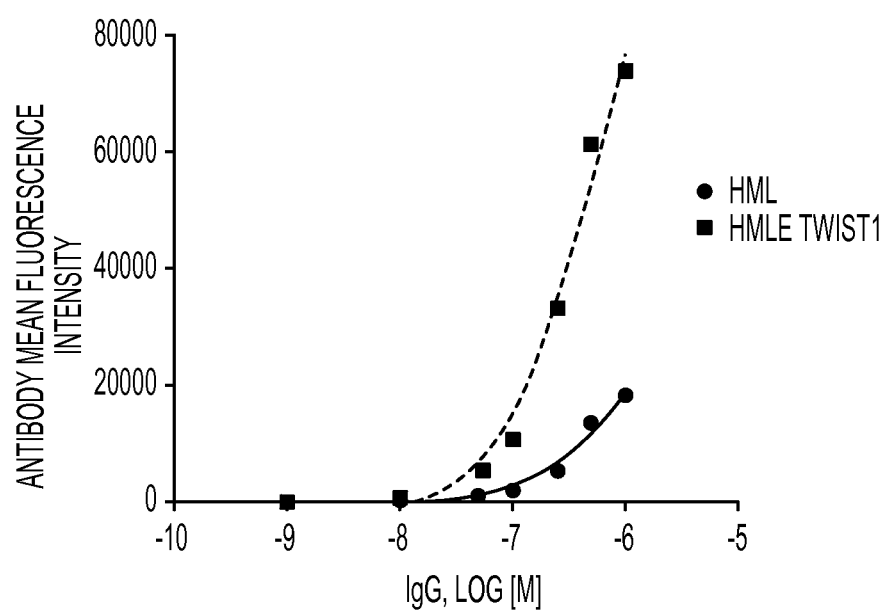
FIG. 8

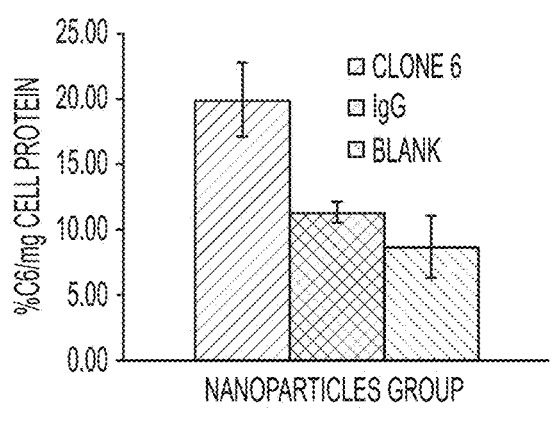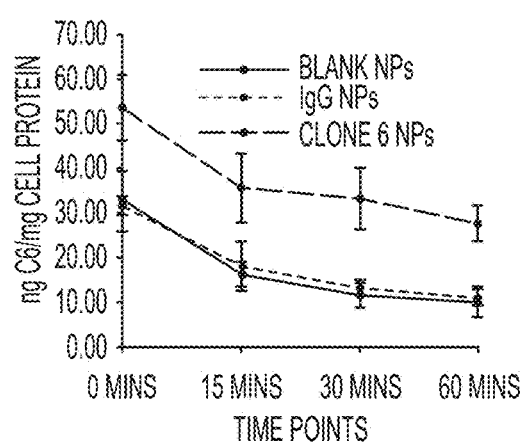
FIG. 15A
FIG. 15B

Heavy Chain vector + insert (variable region underlined)

<u>ATGTACAGGATGCAACTCCTGTCTTGCATTGCACTAAGTCTTGCACTTGTCACGAATTCGGAGG
TGCAGCTGTTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGGAAGGGG
CTGGAGTGGGTCTCAGCGATTAGGGAGGATGGTATTAAGACATATTACGCAGACTCCGTGAAGG
GCCGGTTCACCATCTCCAGAGACAATTCCAAGAACACGCTGTATCTGCAAATGAACAGCCTGAG
AGCCGAGGACACGGCCGTATATTACTGTGCGAAAAGGGCTCGTCGGTTTGACTACTGGGGCCAG
GGAACCCTGGTCACCGTCTCGAGCGCTAGCACCAAGGGCCCATCGGTC</u>TTCCCCCTGGCACCCT
CCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCA
CCCAGACCTACATCTGCAACGTGAATCACAAGCCCAGCAACACCAAGGTGGACAAGAAAGTTGA
GCCCAAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTACGTGGA
CGGCGTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCG
AGAACCACAGGTGTACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATGAGTCCTAG
CTGGCCAGACATGATAAGATACATTGATGAGTTTGGACAAACCACAACTAGAATGCAGTGAAAA
AAATGCTTTATTTGTGAAATTTGTGATGCTATTGCTTTATTTGTAACCATTATAAGCTGCAATA
AACAAGTTAACAACAACAATTGCATTCATTTTATGTTTCAGGTTCAGGGGGAGGTGTGGGAGGT
TTTTTAAAGCAAGTAAAACCTCTACAAATGTGGTATGGAATTAATTCTAAAATACAGCATAGCA
AAACTTTAACCTCCAAATCAAGCCTCTACTTGAATCCTTTTCTGAGGGATGAATAAGGCATAGG
CATCAGGGGCTGTTGCCAATGTGCATTAGCTGTTTGCAGCCTCACCTTCTTTCATGGAGTTTAA
GATATAGTGTATTTTCCCAAGGTTTGAACTAGCTCTTCATTTCTTTATGTTTTAAATGCACTGA
CCTCCCACATTCCCTTTTTAGTAAAATATTCAGAAATAATTTAAATACATCATTGCAATGAAAA
TAAATGTTTTTTATTAGGCAGAATCCAGATGCTCAAGGCCCTTCATAATATCCCCCAGTTTAGT
AGTTGGACTTAGGGAACAAAGGAACCTTTAATAGAAATTGGACAGCAAGAAAGCGAGCTTCTAG
CTTATCCTCAGTCCTGCTCCTCTGCCACAAAGTGCACGCAGTTGCCGGCCGGGTCGCGCAGGGC
GAACTCCCGCCCCCACGGCTGCTCGCCGATCTCGGTCATGGCCGGCCCGGAGGCGTCCCGGAAG
TTCGTGGACACGACCTCCGACCACTCGGCGTACAGCTCGTCCAGGCCGCGCACCCACACCCAGG
CCAGGGTGTTGTCCGGCACCACCTGGTCCTGGACCGCGCTGATGAACAGGGTCACGTCGTCCCG
GACCACACCGGCGAAGTCGTCCTCCACGAAGTCCCGGGAGAACCCGAGCCGGTCGGTCCAGAAC
TCGACCGCTCCGGCGACGTCGCGCGCGGTGAGCACCGGAACGGCACTGGTCAACTTGGCCATGA
TGGCTCCTCCTGTCAGGAGAGGAAAGAGAAGAAGGTTAGTACAATTGCTATAGTGAGTTGTATT
ATACTATGCAGATATACTATGCCAATGATTAATTGTCAAACTAGGGCTGCAGGGTTCATAGTGC
CACTTTTCCTGCACTGCCCCATCTCCTGCCCACCCTTTCCCAGGCATAGACAGTCAGTGACTTA
CCAAACTCACAGGAGGGAGAAGGCAGAAGCTTGAGACAGACCCGCGGGACCGCCGAACTGCGAG
GGGACGTGGCTAGGCCGGCTTCTTTTATCGGTGCGCCGGCCCTCGGAGGCAGGGCGCTCGGGGAG
GCCTAGCGGCCAATCTGCGGTGGCAGGAGGCGGGGCCGAAGGCCGTGCCTGACCAATCCGGAGC
ACATAGGAGTCTCAGCCCCCGCCCCAAAGCAAGGGGAAGTCACGCGCCTGTAGCGCCAGCGTG
TTGTGAAATGGGGCTTGGGGGGGTTGGGGCCCTGACTAGTCAAAACAAACTCCCATTGACGTC
AATGGGGTGGAGACTTGGAAATCCCCGTGAGTCAAACCGCTATCCACGCCCATTGATGTACTGC

FIG. 16A

CAAAACCGCATCATCATGGTAATAGCGATGACTAATACGTAGATGTACTGCCAAGTAGGAAAGT
CCCATAAGGTCATGTACTGGGCATAATGCCAGGCGGGCCATTTACCGTCATTGACGTCAATAGG
GGGCGTACTTGGCATATGATACACTTGATGTACTGCCAAGTGGGCAGTTTACCGTAAATACTCC
ACCCATTGACGTCAATGGAAAGTCCCTATTGGCGTTACTATGGGAACATACGTCATTATTGACG
TCAATGGGCGGGGGTCGTTGGGCGGTCAGCCAGGCGGGCCATTTACCGTAAGTTATGTAACGCC
TGCAGGTTAATTAAGAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCCAA
GCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCTACAC
TAGAAGAACAGTATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGGCTAGTTAATTAACATTTAAATCAGCG
GCCGCAATAAAATATCTTTATTTTCATTACATCTGTGTGTTGGTTTTTTGTGTGAATCGTAACT
AACATACGCTCTCCATCAAAACAAAACGAAACAAAACAAACTAGCAAAATAGGCTGTCCCCAGT
GCAAGTGCAGGTGCCAGAACATTTCTCTATCGAA (SEQ ID NO:3)

Heavy chain variable region protein sequence translation:

MKYLLPTAAAGLLLLAAQPAMAEVQLLESGGGLVQPGGSLRLSCAASGFTFSSYAMSWVRQAP
GKGLEWVSAIREDGIKTYYADSVKGRFTISRDNSKNTLYLQMNSLRAEDTAVYYCAKRARRFD
YWGQGTLVTVS (SEQ ID NO:4)

Light Chain vector + insert          (variable region underlined)

ATGTACAGGATGCAACTCCTGTCTTGCATTGCACTAAGTCTTGCACTTGTCACGAATTCAACGG
ACATCCAGATGACCCAGTCTCCATCCTCCCTGTCTGCATCTGTAGGAGACAGAGTCACCATCAC
TTGCCGGGCAAGTCAGAGCATTAGCAGCTATTTAAATTGGTATCAGCAGAAACCAGGGAAAGCC
CCTAAGCTCCTGATCTATAATGCATCCCTTTTGCAAAGTGGGGTCCCATCAAGGTTCAGTGGCA
GTGGATCTGGGACAGATTTCACTCTCACCATCAGCAGTCTGCAACCTGAAGATTTTGCAACTTA
CTACTGTCAACAGAGTCTGCGTTCGCCTATTACGTTCGGCCAAGGGACCAAGGTGGAAATCAAA
CGTACGGTGGCTGCACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACG
CCTGCGAAGTCACCCATCAGGGCCTGAGCTCGCCCGTCACAAAGAGCTTCAACAGGGGAGAGTG
TTAGAGGGAGCTAGCTCGACATGATAAGATACATTGATGAGTTTGGACAAACCACAACTAGAAT
GCAGTGAAAAAAATGCTTTATTTGTGAAATTTGTGATGCTATTGCTTTATTTGTGAAATTTGTG
ATGCTATTGCTTTATTTGTAACCATTATAAGCTGCAATAAACAAGTTAACAACAACAATTGCAT
TCATTTTATGTTTCAGGTTCAGGGGGAGGTGTGGGAGGTTTTTTAAAGCAAGTAAAACCTCTAC
AAATGTGGTATGGAATTAATTCTAAAATACAGCATAGCAAAACTTTAACCTCAAATCAAGCCT
CTACTTGAATCCTTTTCTGAGGGATGAATAAGGCATAGGCATCAGGGGCTGTTGCCAATGTGCA
TTAGCTGTTTGCAGCCTCACCTTCTTTCATGGAGTTTAAGATATAGTGTATTTTCCCAAGGTTT
GAACTAGCTCTTCATTTCTTTATGTTTTAAATGCACTGACCTCCCACATTCCCTTTTTAGTAAA
ATATTCAGAAATAATTTAAATACATCATTGCAATGAAAATAAATGTTTTTTATTAGGCAGAATC
CAGATGCTCAAGGCCCTTCATAATATCCCCCAGTTTAGTAGTTGGACTTAGGGAACAAAGGAAC

FIG. 16B

```
CTTTAATAGAAATTGGACAGCAAGAAAGCGAGCTTCTAGCTTTAGTTCCTGGTGTACTTGAGGG
GGATGAGTTCCTCAATGGTGGTTTTGACCAGCTTGCCATTCATCTCAATGAGCACAAAGCAGTC
AGGAGCATAGTCAGAGATGAGCTCTCTGCACATGCCACAGGGGCTGACCACCCTGATGGATCTG
TCCACCTCATCAGAGTAGGGGTGCCTGACAGCCACAATGGTGTCAAAGTCCTTCTGCCCGTTGC
TCACAGCAGACCCAATGGCAATGGCTTCAGCACAGACAGTGACCCTGCCAATGTAGGCCTCAAT
GTGGACAGCAGAGATGATCTCCCCAGTCTTGGTCCTGATGGCCGCCCCGACATGGTGCTTGTTG
TCCTCATAGAGCATGGTGATCTTCTCAGTGGCGACCTCCACCAGCTCCAGATCCTGCTGAGAGA
TGTTGAAGGTCTTCATGATGGCTCCTCCTGTCAGGAGAGGAAAGAGAAGAAGGTTAGTACAATT
GCTATAGTGAGTTGTATTATACTATGCTTATGATTAATTGTCAAACTAGGGCTGCAGGGTTCAT
AGTGCCACTTTTCCTGCACTGCCCATCTCCTGCCCACCCTTTCCCAGGCATAGACAGTCAGTG
ACTTACCAAACTCACAGGAGGGAGAAGGCAGAAGCTTGAGACAGACCCGCGGGACCGCCGAACT
GCGAGGGACGTGGCTAGGGCGGCTTCTTTTATGGTGCGCCGGCCCTCGGAGGCAGGGCGCTCG
GGGAGGCCTAGCGGCCAATCTGCGGTGGCAGGAGGCGGGGCCGAAGGCCGTGCCTGACCAATCC
GGAGCACATAGGAGTCTCAGCCCCCGCCCCAAAGCAAGGGGAAGTCACGCGCCTGTAGCGCCA
GCGTGTTGTGAAATGGGGCTTGGGGGGGTTGGGGCCCTGACTAGTCAAAACAAACTCCCATTG
ACGTCAATGGGGTGGAGACTTGGAAATCCCCGTGAGTCAAACCGCTATCCACGCCCATTGATGT
ACTGCCAAAACCGCATCATCATGGTAATAGCGATGACTAATACGTAGATGTACTGCCAAGTAGG
AAAGTCCCATAAGGTCATGTACTGGGCATAATGCCAGGCGGGCCATTTACCGTCATTGACGTCA
ATAGGGGGCGTACTTGGCATATGATACACTTGATGTACTGCCAAGTGGGCAGTTTACCGTAAAT
ACTCCACCCATTGACGTCAATGGAAAGTCCCTATTGGCGTTACTATGGGAACATACGTCATTAT
TGACGTCAATGGGCGGGGGTCGTTGGGCGGTCAGCCAGGCGGGCCATTTACCGTAAGTTATGTA
ACGCCTGCAGGTTAATTAAGAACATGTGAGCAAAAGGCCAGCAAAAGGCCAGGAACCGTAAAAA
GGCCGCGTTGCTGGCGTTTTTCCATAGGCTCCGCCCCCTGACGAGCATCACAAAAATCGACGC
TCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGC
TCCAAGCTGGGCTGTGTGCACGAACCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGC
TACACTAGAAGAACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTGTTTGCAAGCA
GCAGATTACGCGCAGAAAAAAGGATCTCAAGAAGATCCTTTGATCTTTTCTACGGGGTCTGAC
GCTCAGTGGAACGAAAACTCACGTTAAGGGATTTTGGTCATGGCTAGTTAATTAACATTTAAAT
CAGCGGCCGCAATAAAATATCTTTATTTTCATTACATCTGTGTGTTGGTTTTTTGTGTGAATCG
TAACTAACATACGCTCTCCATCAAAACAAAACGAAACAAAACAAACTAGCAAAATAGGCTGTCC
CCAGTGCAAGTGCAGGTGCCAGAACATTTCTCTATCGAA (SEQ ID NO:5)
```

Light chain variable region protein sequence translation:

TDIQMTQSPSSLSASVGDRVTITCRASQSISSYLNWYQQKPGKAPKLLIYNASLLQSGVPSRFS
GSGSGTDFTLTISSLQPEDFATYYCQQSLRSPITFGQGTKVEIKR (SEQ ID NO:6)

FIG. 16C

ANTIBODY FRAGMENTS FOR DETECTING CANCER AND METHODS OF USE

RELATED APPLICATION

This application claims priority to U.S. Provisional Patent Application No. 62/023,354, filed Jul. 11, 2014, the entirety of which is incorporated herein by reference.

SEQUENCE LISTING

The instant application contains a Sequence Listing which has been submitted electronically in ASCII format and is hereby incorporated by reference in its entirety, Said ASCII copy, created on Aug. 11, 2015, is named 09531_395WO1_SL.txt and is 11.5 KB in size.

BACKGROUND OF THE INVENTION

While increased awareness, diagnostic advances and molecularly-targeted therapies have improved breast cancer outcomes, mortality and morbidity remain high. 296,000 new diagnoses and 39,000 fatalities of breast cancer were expected in 2013 in U.S. women. Early detection and screening methods result in a favorable prognostic outlook for women diagnosed with breast cancer. In contrast, patients who present with evidence of metastatic disease have a five-year survival rate of 24% (American Cancer Society, 2014. Cancer Facts & Figures 2014. Atlanta). These statistics indicate that breast cancer can be managed with the current standard of care, when the patient presents with cancer confined to the site of origin. The dramatic reduction in survival rates upon evidence of metastasis suggests an urgent need to focus on the development of therapies/technologies designed to detect and eliminate metastatic cancer.

Accordingly, there exists the need for new reagents for the detection and treatment of cancer, in particular, therapies and reagents capable of effecting therapeutic and diagnostic benefits.

SUMMARY OF THE INVENTION

The present invention provides in certain embodiments an immune reagent comprising a first scFv antibody fragment (26-29 kDa) that specifically binds to membrane protein HSPG2 (Perlecan).

In certain embodiments, the immune reagent further comprises a second scFv antibody fragment operably linked to the first scFv antibody fragment (52-60 kDa) to form a diabody. In certain embodiments, the second scFv antibody fragment specifically binds to membrane protein HSPG2 (Perlecan).

In certain embodiments, the first and/or second antibody fragment has 90% identity to the amino acid sequence of Clone-6 (FIG. 7). In certain embodiments, the first and/or second antibody fragment has 90%, 91%, 92%, 93%, 94%, 95%, 96%, 97%, 98%, 99% or 100% identity to the amino acid sequence of Clone-6 (FIG. 7). In certain embodiments, both the first and second scFv antibody fragments are Clone-6. In certain embodiments, the immune reagent comprises a heavy chain encoded by a nucleic acid having at least 90% identity to SEQ ID NO:3 and a light chain encoded by a nucleic acid having at least 90% identity to SEQ ID NO:5.

In certain embodiments, the immune reagent comprises a heavy chain variable region having at least 90% identity to SEQ ID NO:4 and a light chain variable region having at least 90% identity to SEQ ID NO:6.

In certain embodiments, the immune reagent comprises a heavy chain variable region having 100% identity to SEQ ID NO:4 and a light chain variable region having 100% identity to SEQ ID NO:6.

In certain embodiments, the immune reagent comprises a first immune reagent described above operably linked to a second immune reagent described above.

In certain embodiments, the first and second antibody fragments are linked by means of a linker. In certain embodiments, the linker is a peptide linker. In certain embodiments, the peptide linker is 3 to 25 amino acid residues in length. In certain embodiments, the linker is between 3 and 12 amino acids in length.

In certain embodiments, the linker is a chemical linker.

In certain embodiments, the immune reagent of any one of claims 1-9, further comprising a poly-His tail operably linked to either the first or second antibody fragment.

The present invention provides in certain embodiments a nucleic acid encoding the diabody described above.

The present invention provides a nucleic acid encoding SEQ ID NO:3.

The present invention provides a nucleic acid encoding SEQ ID NO:4.

In certain embodiments, the nucleic acid further comprises a promoter to form an expression cassette.

The present invention provides in certain embodiments a vector comprising the expression cassette described above.

The present invention provides in certain embodiments a cell comprising the nucleic acid, expression cassette, or the vector described above.

The present invention provides in certain embodiments a conjugate comprising the immune reagent described above conjugated to a detection agent and/or a therapeutic agent. In certain embodiments the conjugate comprising the immune reagent described above is conjugated to a detection agent. In certain embodiments the conjugate comprising the immune reagent described above is conjugated to a therapeutic agent (e.g., a cytotoxic compound). In certain embodiments the conjugate comprising the immune reagent described above is conjugated to a detection agent and a therapeutic agent.

In certain embodiments, the detection agent and/or therapeutic agent includes a radionuclide. In certain embodiments, the radionuclide is metallic. In certain embodiments, the radionuclide is selected from Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

In certain embodiments, the detection agent comprises a fluorescent group. In certain embodiments, the fluorescent group is fluorescein, tetrachlorofluorescein, hexachlorofluorescein, tetramethylrhodamine, rhodamine, cyanine-derivative dyes, Texas Red, Bodipy, and/or Alexa dye.

In certain embodiments, the therapeutic agent is a cytotoxic compound. In certain embodiments the therapeutic agent a chemotherapeutic agent. In certain embodiments, the chemotherapeutic agent is selected from all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, and/or tyrosine kinase inhibitors. In certain embodiments, the tyrosine kinase inhibitor is Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib and/or Vandetanib.

The present invention provides in certain embodiments a pharmaceutical composition comprising the immune reagent or the conjugate described above and a pharmaceutically acceptable excipient.

In certain embodiments, the composition compriswa an immune agent, conjugate and/or the pharmaceutical composition described above operably linked to a carrier. In certain embodiments, the carrier is a nanoparticle or liposome. In certain embodiments, the nanoparticle is a polymeric nanoparticle, micellar system and/or nanocapsule, inorganic nanoparticle such as iron oxide nanoparticle, quantum dot or silica nanoparticle, polymer-based system such as dendrimer and/or polymer drug conjugate.

The present invention provides in certain embodiments a method for detecting cancer in an animal comprising administering a therapeutically effective amount of a conjugate described above to the animal. In certain embodiments, the cancer is melanoma, breast cancer or prostate cancer.

The present invention provides in certain embodiments a method for treating or preventing cancer in an animal comprising administering a therapeutically effective amount of an immune reagent or conjugate described above to the animal. In certain embodiments, the cancer is melanoma, breast cancer or prostate cancer. In certain embodiments, the cancer is breast cancer.

The present invention provides in certain embodiments an immune reagent or a conjugate described above for use in medical therapy.

The present invention provides in certain embodiments an immune reagent or a conjugate described above for the prophylactic or therapeutic treatment of cancer.

The present invention provides in certain embodiments the use of an immune reagent of or a conjugate described above to prepare a medicament for treating cancer in an animal.

The present invention provides in certain embodiments a method of detecting a HSPG2, comprising contacting a cell with an immune reagent or a conjugate described above.

The present invention provides in certain embodiments a method of detecting cancer cells in a test tissue sample, comprising contacting the test sample with a conjugate of any one of claims 15-19 and measuring a signal from the detection agent, wherein a signal from the test sample that is greater than a signal from a non-cancerous control sample indicates the presence of cancer cells in the test tissue sample. In certain embodiments, signal from the test sample is 1-100% greater than the signal from the control sample.

The present invention provides in certain embodiments a method of detecting cancer in an animal (e.g., a human), comprising administering a conjugate described above to the animal and measuring a signal from the detection agent, wherein a signal greater than a signal from a control animal without cancer indicates the animal has cancer. In certain embodiments, the signal from the animal is 1-100% greater than the signal from the control animal. In certain embodiments, the signal from the detection agent is measured using PET imaging.

The present invention provides in certain embodiments a method of determining the effectiveness of a cancer therapy in an animal, comprising (a) administering a conjugate described above to the animal and measuring a first signal (e.g., a radioactive signal) from the detection agent; (b) administering a cancer therapy; (c) administering a conjugate described above to the animal and measuring a second signal (e.g., a radioactive signal) from the detection agent; and (d) comparing the first signal with the second signal, wherein the cancer therapy is effective if the second signal is less than the first signal.

In certain embodiments, second signal is 1-100% less than the first signal.

In certain embodiments, first and second signals are measured using PET imaging.

The present invention provides in certain embodiments a kit comprising (a) an immune reagent described above; (b) instructions for conjugating a radionuclide to the immune reagent to generate a radiolabeled conjugate; and (c) instructions for administering the radiolabeled conjugate to an animal. In certain embodiments, the kit further comprises a radionuclide.

BRIEF DESCRIPTION OF DRAWINGS

FIGS. 6A-6E. LM2 cells were grafted orthotopically in Balb/c nude mice. Four weeks after tumor induction, mice were euthanized, and blood collected by cardiac puncture. Following density gradient centrifugation to isolate mononuclear cells (PBMCs) and potential circulating tumor cells, erythrocytes were lysed, and samples from animals bearing LM2 tumors were pooled and divided into three equal fractions for labelling with 50 nM Alexa-647 labelled Diabody or Pacific blue labelled IgG EpCAM antibody. Non-tumor bearing mouse blood was collected for use as controls. (A) Control PBMCs from non-tumor bearing mice were used to establish fluorescent gating parameters. Population P1 is defined in the left panel as green fluorescent positive events. Note that LM2 cells are GFP stable. The right panel analyzes Pac-Blue EpCAM on the X-axis and Alexa-647 Diabody on the Y-Axis, in P1 gated events. (B) LM2 cells spiked into control PBMCs immediately prior to analysis are used to establish population P1 based on GFP expression. (C) Cells from the blood of tumor bearing mice singly stained for Alexa-647 Diabody. (D) Cells from the blood of tumor bearing mice singly stained for EpCAM Pacific blue (E) Cells from the blood of tumor bearing mice singly stained for Alexa-647 Diabody and EpCAM Pacific blue.

FIG. 7. Nucleic acid and amino acid sequences for antibody fragment Clone 6 scFv.

FIG. 8. Binding titration curves of phage display derived IgG1 targeting HMLE-Twist1 cells. An scFv phage display library was used to identify candidate clones capable of selective binding to HMLE-Twist1 cells. Candidate scFv were subsequently reformatted to human IgG1 antibodies (A) binding of candidate clone (Tw1S4_6 IgG) to triple negative breast cancer cell lines, as assessed by flow cytometry. $1*10^5$ cells were incubated in suspension with indicated IgG concentration. Detection of IgG labelled cells was confirmed with anti-human IgG Dylight 647 secondary antibody on a digital flow cytometer (B) Binding titration curves for candidate clone Tw1S4_6 IgG to HMLE and HMLE-Twist1 cells demonstrates selective affinity of HMLE-Twist1 cells.

FIGS. 15A-15B. Conjugation of Tw1S4_6 IgG (Clone 6) to polymeric nanoparticles enhances the uptake (A) and retention (B) of the nanoparticles. (A) MDA-MB-231-LM2 cells were incubated with nanoparticles conjugated to Tw1S4_6 IgG (Clone 6), nanoparticles conjugated to a non-targeting isotype antibody control (IgG) or nanoparticles without any antibody conjugation (blank) at 4° C. After 1 hour, the media was replaced with fresh serum containing media. Cells were then placed at 37° C. for 4 hours. Finally, cells were washed and lysed. Samples were analyzed for the dye-label (6-coumarin) by HPLC. The amount of nanoparticles in the cells was normalized to the total cell protein. (B) MDA-MB-231-LM2 cells were incubated with nanoparticles at 37° C. for 2 hours. At the end of 2 hours, cells were washed, incubated with fresh medium, and lysed at 0, 15, 30 and 60 minutes. Samples were analyzed for the dye-label (6-coumarin) by HPLC. The amount of nanoparticles in the cells was normalized to the total cell protein.

FIGS. 16A-16C. Nucleic acid sequence of heavy chain vector and insert (variable region underlined), (SEQ ID NO:3), Amino acid sequence of the heavy chain variable region, (SEQ ID NO:4), Nucleic acid sequence of light chain vector and insert (variable region underlined) (SEQ ID NO:5), and Amino acid sequence of the light chain variable region (SEQ ID NO:6).

DETAILED DESCRIPTION OF THE INVENTION

Figure 1A:
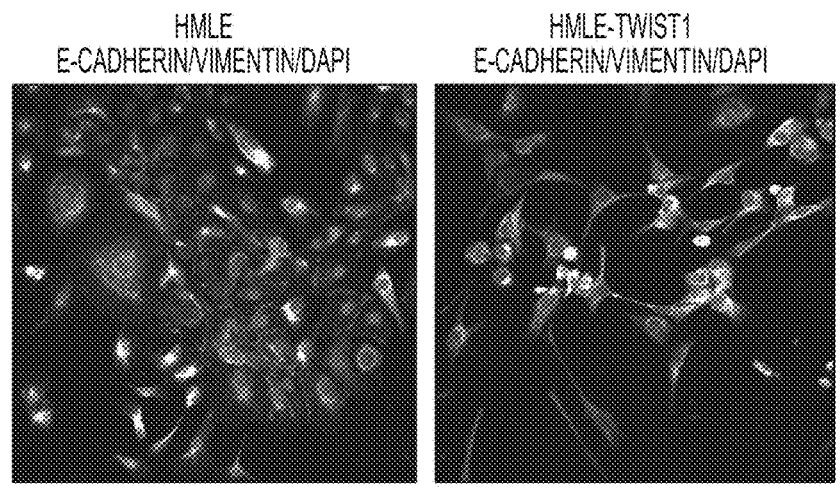
FIGS. 1A-1C. EMT Characteristics of isogenic cell lines. (A) Immunofluorescence staining of HMLE and EMT transitioned HMLE-Twist1 cells for canonical epithelial and mesenchymal protein markers E-Cadherin and Vimentin, respectively. (B) Dose-response curve showing differential sensitivity of HMLE and HMLE-Twist1 cells to conventional chemotherapeutic agent paclitaxel. (C) Cell surface cancer stem cell immunophenotyping demonstrates HMLE-Twist1 is predominately CD44+/CD24 low (right panel), relative to HMLE cells which have a mixed phenotype. Note CD44 hi/CD24 low represents the breast cancer stem cell like phenotype.

Epithelial to mesenchymal transition (EMT) in metastatic breast cancer: the idea of metastatic dissemination as a late stage event in tumor progression has been challenged recently, as emerging evidence suggests an early appearance in tumorigenesis. Conventional diagnosis of metastatic cancer entails detection of regional lymph node dissemination, yet 20-40% of lymph node negative patients are believed to harbor occult metastases in bone marrow, and other distant sites, at the time of diagnosis. Metastasis of breast carcinoma includes invasion, intravasation into circulation, survival, extravasation out of the circulation, and seeding of distant mi-crometastatic lesions. The key cellular/molecular events that give rise to metastatic dissemination in breast cancer begin as a histological transition from carcinoma in situ to invasive carcinoma. Release of cytokines, growth factors, and matrix proteases by inflammatory cells, endothelial cells, and resident fibroblasts of activated tumor stroma leads to dissolution of basement membrane that contain benign neoplastic lesions. Tumor cell interaction with the stroma then produces profound morphogenetic changes in neoplastic epithelial cells. These changes manifest as a loss of the polarized, cell-cell adhesion characteristics of epithelial cells, and acquisition of motile, invasive fibroblast-like characteristics. This process, termed EMT, plays a critical role in the generation of circulating tumor cells (CTCs) and eventual metastasis by generating invasive carcinoma cells that enter the circulation seed distant metastases.

Recent technological advances have enabled clinicians to obtain immediate evidence of metastatic dissemination via enumeration of CTCs in peripheral blood of patients. While numerous CTC detection technologies exist at various stages of pre-clinical development (Xu, R., and Mao, J.-H. 2011. Gene transcriptional networks integrate microenvironmental signals in human breast cancer. *Integrative Biology* 3:368-374), CELLSEARCH is the only method currently approved by the FDA for this purpose. Using this technology, a cutoff of five CTCs per 7.5 mL blood was able to predict good vs. poor prognosis in metastatic breast cancer patients (Yang, J., Mani, S. A., and Weinberg, R. A. 2006. Exploring a New Twist on Tumor Metastasis. *Cancer research* 66:4549-4552). CTC enumeration now has established prognostic value in both early stage and advanced breast cancer (Yang, J., Mani, S. A., and Weinberg, R. A. 2006. Exploring a New Twist on Tumor Metastasis. *Cancer research* 66:4549-4552). Concerns have been raised, however, regarding the method of CTC capture using CELLSEARCH, which is reliant upon an antibody directed against the epithelial cell adhesion molecule (EpCAM). The critical assumption of the CELLSEARCH platform is that CTCs will express EpCAM, owing to the fact that the cell of origin in carcinoma is epithelial. However, the key cellular event that gives rise to CTCs is the acquisition of an invasive EMT phenotype within the primary tumor. This phenotypic change manifests as a loss of the polarized, cell-cell adhesion characteristics of epithelial cells, and is accompanied by increased motility and invasiveness (Pantel, K., Müller, V., Auer, M., Nusser, N., Harbeck, N., and Braun, S. 2003. Detection and Clinical Implications of Early Systemic Tumor Cell Dissemination in Breast Cancer. *Clinical Cancer Research* 9:6326-6334). A number of recent studies have demonstrated EMT marker gene expression in CTCs of breast cancer patients. Importantly, studies employing CTC enumeration as a means to monitor therapeutic response have demonstrated that CTCs identified at follow-up are enriched for EMT marker gene expression (Patani, N., and Mokbel, K. 2011. Clinical significance of sentinel lymph node isolated tumour cells in breast cancer. *Breast Cancer Research and Treatment* 127:325-334; Bonnomet, A., Brysse, A., Tachsidis, A., Waltham, M., Thompson, E., Polette, M., and Gilles, C. 2010. Epithelial-to-Mesenchymal Transitions and Circulating Tumor Cells. *Journal of Mammary Gland Biology and Neoplasia* 15:261-273). These findings suggest that the full complement of CTCs is not being effectively monitored or characterized with existing CTC technologies that rely solely on epithelial marker expression.

The CELLSEARCH system is comprised of two components in series: the CellTracks autoprep fluidics system and the CellTracks analyzer. The autoprep is an automated fluidics system for immunomagnetic enrichment of CTCs, employing ferrofluids conjugated to antibodies targeting EpCAM. The CellTracks analyzer is a semi-automated fluorescence microscopy station. Immunocytochemistry is used to characterize the captured CTCs for lymphocyte marker exclusion (CD45) and Cytokeratin expression, to confirm CTCs are of epithelial origin. The reliance on a positive selection step (EpCAM magnetic beads) to enrich for CTCs results in a sample of high purity. However, owing to the exceedingly rare occurrence of CTCs in blood, many events with low to intermediate expression, such as EMT+ CTCs, are missed.

Certain embodiments of the present invention provide a nucleic acid encoding a antibody or antibody fragment described above. In certain embodiments, the nucleic acid further comprises a promoter. Examples include, but are not limited to, a lac promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In certain embodiments, other control elements, such as enhancers and the like, will be of particular use. In certain embodiments, a gIII signal sequence is included at the 5' terminus. In certain embodiments, the nucleic acid further comprises a nucleic acid encoding, a c-myc tag and a nucleic acid encoding a $(His)_6$ to tag SEQ ID NO: 7) that are positioned in-frame at the 3' terminal of the bispecific antibody. The gIII signal sequence directs the polypeptide into the periplasmic space, where it can fold correctly in a soluble form. The c-myc tag is used to analyze the expression level of the bispecific scFv, and $(His)_6$ tag (SECS ID NO: 7) can be used to purify the bispecific scFy protein.

Certain embodiments of the present invention provide an expression cassette comprising the nucleic acid sequence described above and a promoter.

Certain embodiments of the present invention provide a vector comprising the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

Certain embodiments of the present invention provide the vector or expression cassette described above.

Certain embodiments of the present invention provide a therapeutic composition comprising a bispecific antibody described above, in combination with a physiologically-acceptable, non-toxic vehicle.

Cancer

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and melanoma.

Antibodies and Antibody Fragments

Certain Embodiments of the Present Invention Provide an Immune Reagent Comprising a First scFv antibody fragment that specifically binds to membrane protein HSPG2 (Perlecan).

As used herein, the term "antibody" includes scFv, humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv or "nanobody"), humanized, fully human or chimeric antibodies, full length antibodies, single-chain antibodies, diabodies, and antigen-binding fragments of antibodies (e.g., Fab fragments). A scFv is a fusion protein of the variable region of the heavy ($V_H$) and light chains ($V_L$) of an immunoglobulin that is connected by means of a linker. In certain embodiments, the linker between the $V_H$ and $V_L$ is a peptide. In certain embodiments, the linker is short, about 3-25 amino acids in length. In certain embodiments the linker is about 3-12 amino acids in length. If flexibility is important, the linker will contain a significant number of glycines. If solubility is important, serines or threonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. In certain embodiments, the linker that is used to link the two scFv moieties is a peptide. In certain embodiments, the linker is short, about 3-25 amino acids in length.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as *E. coli*, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12:

98-105 (1982); U.S. Pat. No. 3,773,919; EP Patent Application No. 58,481; Sidman et al., Biopolymers 22: 547-556 (1983); EP: 133,988).

Nucleic Acid Molecules Encoding Antibodies

The present invention further provides nucleic acid sequences that encode the antibodies described above.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed base and/or deoxyinosine residues (Batzer et al., Nucl. Acids Res., 19:508 (1991); Ohtsuka et al., JBC, 260:2605 (1985); Rossolini et al., Mol. Cell. Probes, 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The terms "protein," "peptide" and "polypeptide" are used interchangeably herein.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, CABIOS, 4:11 (1988); the local homology algorithm of Smith et al., Adv. Appl. Math., 2:482 (1981); the homology alignment algorithm of Needleman and Wunsch, JMB, 48:443 (1970); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990), modified as in Karlin and Altschul, Proc. Natl. Acad. Sci. USA, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994). The ALIGN program is based on the algorithm of Myers and Miller, supra. The BLAST programs of Altschul et al., JMB, 215: 403 (1990); Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm. nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, and at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein.

Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

Linkers

In certain embodiments, the antibody is linked to a detection agent (e.g., fluorophore) by means of a linker.

In certain embodiments, an aliphatic or ethylene glycol linker (as are well known to those will skill in the art) is used. In certain embodiments, the linker is a phosphodiester linkage. In certain embodiments, the linker is a phosphorothioate linkage. In certain embodiments, other modified linkages between the modifier groups like dyes and quencher and the bases are used in order to make these linkages more stable, thereby limiting degradation to the nucleases.

In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin.

In certain embodiments, the antibody is linked to the detection agent by means of a covalent bond.

In certain embodiments, the antibody probe, i.e., an antibody that is operably linked to a detection agent, is also operably linked to a solid substrate. For example, the antibody probe may be linked to a magnetic bead.

Chemistries that can be used to link the detection agent to the antibody are known in the art, such as disulfide linkages, amino linkages, covalent linkages, etc. In certain embodiments, aliphatic or ethylene glycol linkers that are well known to those with skill in the art can be used.

Detection and Therapeutic Compositions

In certain embodiments, the immune reagents described above can be prepared as pharmaceutically-acceptable compositions. In certain embodiments, the immune reagents are administered so as to result in the detection of a cancer. In certain embodiments, the immune reagents are administered so as to result in the treatment of a cancer. The amount administered will vary depending on various factors including, but not limited to, the composition chosen, the particular disease, the weight, the physical condition, and the age of the mammal. Such factors can be readily determined by the clinician employing animal models or other test systems, which are well known to the art.

In certain embodiments, the antibody is conjugated to a therapeutic compound, such as a cytotoxic compound. Methods of conjugating antibodies to compounds is known in the art (see, e.g., Behrens et al., "Methods for site-specific drug conjugation to antibodies," mAbs 6(1):46-53 (2014); Anderl et al., "Antibody-drug conjugate payloads," Laurent Ducry (ed.), Antibody-Drug Conjugates, Methods in Molecular Biology, vol. 1045:51-70 (2013)). In certain embodiments, the therapeutic compound is conjugated to the diabody by means of a maleimide-thiol linkage through cysteines on the immune reagent.

In certain embodiments, the immune reagent is operably linked to one or more chemotherapeutic agent. In certain embodiments, the chemotherapeutic agent is selected from all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, and/or tyrosine kinase inhibitors. In certain embodiments, the tyrosine kinase inhibitor can include Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib and/or Vandetanib.

In certain embodiments, the immune reagent is operably linked to a nanoparticle. In certain embodiments, the nanoparticle is a polymeric nanoparticle, micellar system and/or nanocapsule, inorganic nanoparticle such as iron oxide nanoparticle, quantum dot or silica nanoparticle, polymer-based system such as dendrimer and/or polymer drug conjugate.

Treatment, Detection and Diagnostic Methods

Certain embodiments of the invention provide a pharmaceutical composition comprising an immune reagent, antibody or antibody fragment and a pharmaceutically acceptable excipient.

Certain embodiments of the invention provide a method for treating or preventing cancer in an animal (e.g., a human) comprising administering a therapeutically effective amount of an immune reagent, antibody or antibody fragment to the animal.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The invention also provides an antibody specific for HSPG2 (Perlecan) for use in medical therapy.

The invention also provides an antibody specific for HSPG2 (Perlecan) for the prophylactic or therapeutic treatment of cancer.

The invention also provides the use of an antibody specific for HSPG2 (Perlecan) to prepare a medicament for treating cancer in an animal (e.g. a mammal such as a human).

In certain embodiments, the cancer is melanoma, breast cancer or prostate cancer.

In certain embodiments, the cancer is breast cancer.

Certain embodiments of the invention provide a method of detecting a HSPG2 (Perlecan) molecule, comprising contacting a cell with an immune reagent, antibody or antibody fragment specific for HSPG2. Certain embodiments of the invention provide a method of detecting a circulating tumor cell comprising contacting a cell with an immune reagent, antibody or antibody fragment specific for HSPG2. In certain embodiments, the detection agent comprises a chelating group labeled with a radionuclide. In certain embodiments, the detection agent comprises a fluorescent group. In certain embodiments, the method further comprises quantifying the concentration of HSPG2 on the surface of the cell by measuring a signal from the detection agent (e.g., a fluorescent signal or a radioactive signal).

Certain embodiments of the invention provide a method of detecting cancer cells in a test tissue sample, comprising contacting the test sample with an antibody specific for HSPG2 and measuring a signal from the detection agent (e.g., a radioactive signal or fluorescent signal), wherein a signal greater than a signal from a non-cancerous control sample indicates the presence of cancer cells in the test tissue sample. In certain embodiments, the signal from the test sample is 1-100% greater than the signal from the control sample. In certain embodiments, the signal from the test sample is 10%, 20%, 30%, 40%, 50%, 60%, 70%, 80%, or 90% greater than the signal from the control sample.

Certain embodiments of the invention provide an in vivo method of detecting cancer in an animal (e.g., a human patient), comprising administering an antibody specific for HSPG2 to the animal and measuring a signal (e.g., a radioactive signal or fluorescent signal emitting in the near infrared range) from the detection agent, wherein a signal greater than a signal from a control animal without cancer indicates the animal has cancer. Certain embodiments of the invention provide a method of detecting a circulating tumor cell comprising contacting a cell with an immune reagent, antibody or antibody fragment specific for HSPG2. In certain embodiments, the signal from the animal is 1-100% greater than the signal from the control animal. In certain embodiments, the signal from the animal is 10%, 20%, 30%, 40%, 50%, 60%, 70%, 80%, or 90% greater than the signal from the control animal. In certain embodiments of the invention, the signal from the detection agent is measured using PET imaging or MRI.

Certain embodiments of the invention provide a method for determining the effectiveness of a cancer therapy in an animal (e.g., a human patient), comprising (1) administering an antibody specific for HSPG2 to the animal and measuring a first signal (e.g., a radioactive signal or fluorescent signal emitting in the near infrared range) from the detection agent; (2) administering a cancer therapy; (3) administering an antibody specific for HSPG2 to the animal and measuring a second signal (e.g., a radioactive signal or fluorescent signal emitting in the near infrared range) from the detection agent; and (4) comparing the first signal with the second signal, wherein the cancer therapy is effective if the second signal is less than the first signal.

In certain embodiments, the second signal is 1-100% less than the first signal. In certain embodiments, the first signal is 10%, 20%, 30%, 40%, 50%, 60%, 70%, 80%, or 90% less than the first signal. In certain embodiments of the invention, the signal from the detection agent is measured using PET imaging or by MRI. In certain embodiments of the invention, the signal from the detection agent is measured using PET imaging.

Certain embodiments of the invention provide a kit comprising: (1) an antibody specific for HSPG2; and (2) instructions for administering the antibody to an animal.

Certain embodiments of the invention provide a kit comprising: (1) an antibody specific for HSPG2; (2) instructions for conjugating a radionuclide to the antibody to generate a radiolabeled conjugate; and (3) instructions for administering the radiolabeled conjugate to an animal.

Certain embodiments of the invention provide a kit comprising: (1) an antibody specific for HSPG2; (2) a radionuclide; (3) instructions for conjugating the radionuclide to the antibody to generate a radiolabeled conjugate; and (4) instructions for administering the radiolabeled conjugate to an animal.

Administration

The antibody specific for HSPG2 can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present antibodies may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the conjugates may be combined with one or more excipients and used in the form of ingestible tablets, buccal tablets, troches, capsules, elixirs, suspensions, syrups, wafers, and the like. Such compositions and preparations should contain at least 0.1% of conjugates. The percentage of the compositions and preparations may, of course, be varied and may conveniently be between about 2 to about 60% of the weight of a given unit dosage form. The amount of the conjugates in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the conjugates, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the conjugates may be incorporated into sustained-release preparations and devices.

The conjugates may also be administered intravenously or intraperitoneally by infusion or injection. Solutions of the conjugates can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

In certain embodiments, an antibody specific for HSPG2 is operably linked to a detection agent, wherein the detection agent comprises a chelating group labeled with a radionuclide, is formulated for administration by infusion.

The pharmaceutical dosage forms suitable for injection or infusion can include sterile aqueous solutions or dispersions or sterile powders comprising the conjugates which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the conjugates in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the conjugates plus any additional desired ingredient present in the previously sterile-filtered solutions.

For topical administration, the present conjugates may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present conjugates can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the antibody specific for HSPG2 can be determined by comparing their in vitro activity, and in vivo activity in animal models. Methods for the extrapolation of effective dosages in mice, and other animals, to humans are known to the art; for example, see U.S. Pat. No. 4,938,949.

The amount of the conjugates, or derivative thereof, required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Conjugates of the invention can also be administered in combination with other therapeutic agents, for example, other agents that are useful for the treating cancer. Examples of such agents include chemotherapeutic agents. Accordingly, one embodiment the invention also provides a composition comprising an antibody specific for HSPG2, at least one other therapeutic agent, and a pharmaceutically acceptable diluent or carrier. The invention also provides a kit comprising an antibody specific for HSPG2, at least one other therapeutic agent, packaging material, and instructions for administering an antibody specific for HSPG2 and the other therapeutic agent or agents to an animal to treat cancer.

The invention will now be illustrated by the following non-limiting Examples.

EXAMPLE 1

Circulating tumor cell (CTC) detection has emerged as an important new diagnostic procedure for patients with metastatic tumors. However, fundamental questions still remain as to the precise genetic and phenotypic background of CTCs. The only FDA-approved CTC analysis system, CELLSEARCH®, relies on an initial enrichment step to isolate CTCs from whole blood using anti-EpCAM antibody coated magnetic beads. Many studies now demonstrate that a majority of CTCs are negative for expression of EpCAM, and that these EpCAM negative CTCs may be more metastatically virulent.

The CELLSEARCH is the only FDA approved medical device for use in clinical analysis of CTCs. It is not, however, currently recommended for use as a molecular marker in any form of solid tumor by either the American Society of Clinical Oncology (ASCO) or the National Comprehensive Cancer Network (NCNN) (Malhotra, G. K., Zhao, X., Band, H., and Band, V. 2010. Histological, molecular and functional subtypes of breast cancers. *Cancer Biology & Therapy* 10:955-960; Kalluri, R., and Zeisberg, M. 2006. Fibroblasts in cancer. *Nature reviews. Cancer* 6:392-401). The current utility of CELLSEARCH is to aid in prognosis of metastatic breast, colon and prostate cancer patients (Tsuji, T., Ibaragi, S., Shima, K., Hu, M. G., Katsurano, M., Sasaki, A., and Hu, G.-f. 2008. Epithelial-Mesenchymal Transition Induced by Growth Suppressor p12CDK2-AP1 Promotes Tumor Cell Local Invasion but Suppresses Distant Colony Growth. *Cancer research* 68:10377-10386), and is used sporadically at the discretion of the clinician. The overarching goal of the CTC enumeration field, and a prerequisite for its recommendation for use, is to extend the utility of this technology beyond prognosis and into informing patient management. Lack of recommendations from clinical governing bodies concerning implementation of CELLSEARCH is the result of there being no current demonstration, via clinical trial, of CELLSEARCH being an effective tool to inform patient management. The Southwest Oncology Group (SWOG) S0500 trial was designed to evaluate the utility of CELLSEARCH in determining whether metastatic breast cancer patients with elevated CTC counts at first follow-up, would benefit from changing therapeutic agent. The results are yet to be published but were presented this past December at the San Antonio Breast Cancer Symposium. CTC analysis was found not to be a good molecular indicator in determining whether therapy adjustments would benefit the patient.

While the results of the SWOG trial predict a tenuous future for CELLSEARCH, an analogous study was performed with 40 metastatic breast cancer patients, by Toner and colleagues. Using a custom fluidics platform that captures CTCs expressing both mesenchymal and epithelial specific markers, they were able to demonstrate dynamic phenotypic changes in CTCs in response to therapeutic regimen. Patients who responded well to therapy had CTCs with epithelial markers, whereas progressive disease was accompanied by predominately mesenchymal CTCs (Tsuji, T., Ibaragi, S., Shima, K., Hu, M. G., Katsurano, M., Sasaki, A., and Hu, G.-f. 2008. Epithelial-Mesenchymal Transition Induced by Growth Suppressor p12CDK2-AP1 Promotes Tumor Cell Local Invasion but Suppresses Distant Colony Growth. *Cancer research* 68:10377-10386). Further evidence supporting the need to enumerate mesenchymal CTCs comes from Marchetti and colleagues. They established adherent cell lines from CTCs isolated from breast cancer patients, following a multi-parameter flow cytometry-based cell sorting protocol. Sorted CTCs, based on a brain metastasis gene signature, efficiently formed brain and lung metastases in experimental mouse models of metastasis. It is critical to note that EpCAM expression was absent in these cell populations (Brabletz, T., Jung, A., Spaderna, S., Hlubek, F., and Kirchner, T. 2005. Migrating cancer stem cells [mdash] an integrated concept of malignant tumour progression. *Nat Rev Cancer* 5:744-749). Thus, if CTC enumeration is to become an effective tool to inform patient management, mesenchymal-like CTCs must be included in the initial capture step. The goal of this project is to validate a CTC immunocapture reagent that is capable of capturing mesenchymal CTCs in pilot clinical studies. We envision this approach being coupled to EpCAM based immunocapture in future to insure that the full complement of CTCs is being enumerated.

The key cellular event that likely gives raise to CTCs is the acquisition of an invasive mesenchymal phenotype within the primary tumor, mediated by the epithelial-to-mesenchymal transition (EMT). During EMT, partial to full loss of epithelial characteristics accompanies an invasive phenotype. The goal of this project is to develop an immunocapture reagent for mesenchymal CTCs in triple negative breast cancer. In pursuit of this goal, we have identified a single chain Fv (scFv; 'clone 6') capable of selective binding to EM transitioned, immortalized human mammary epithelial tumor cells. We have engineered the linker length of clone 6 to facilitate stable homodimerization, or 'diabody' formation. The diabody of clone 6 displays dramatically improved functional cell binding relative to the monovalent scFv. Furthermore, our studies show that clone 6 diabody is capable of binding CTCs in a mouse xenograft model of human metastatic breast cancer. Its target antigen, HSPG2, represents a potentially unique cell surface biomarker of mesenchymal CTCs. When used in conjunction with the conventional IgG EpCAM magnetic capture, we envision bivalent clone 6 as providing a highly complementary approach to capture the full suite of CTCs to be enumerated. In addition to the CTC diagnostic application, we expect that HSPG2 will also be a useful therapeutic target. Future studies will evaluate clone 6-conjugated drugs or drug carriers for specific targeting of metastases. Thus, the overall impact of this research is expected to broad and significant.

Figure 1B:
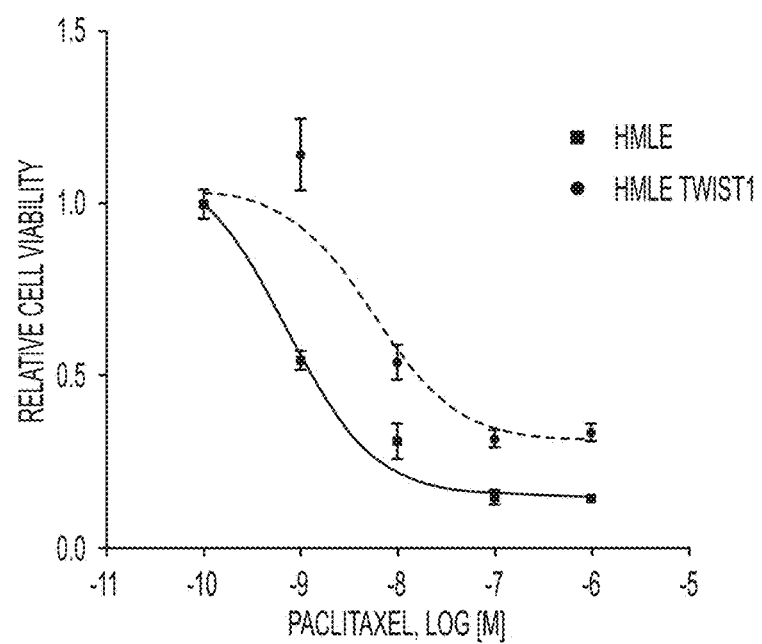
Figure 1C:
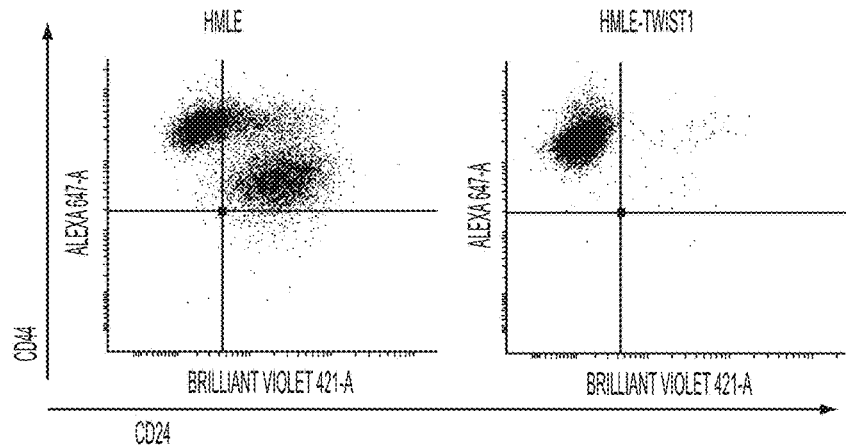

To accomplish our goal of identifying an antibody suitable for immunocapture of mesenchymal CTCs, we developed an in vitro competition based bio-panning procedure, employing a commercially available phage display library. The phage display library was developed to display scFv domains in monovalent format, on the surface of bacteriophage (Millner, L. M., Linder, M. W., and Valdes, R., Jr. 2013. Circulating tumor cells: a review of present methods and the need to identify heterogeneous phenotypes. *Annals of Clinical and Laboratory Science* 43:295-304). For the biopanning procedure, an isogenic matched mammary epithelial cell line pair was employed (HMLE, control mammary epithelial cells, and HMLE-Twist1, an EMT phenotypic cell line). These cells were a generous gift from the lab of Dr. Robert Weinberg, and have been previously characterized in a seminal paper demonstrating that EMT is accompanied by acquisition of a highly aggressive phenotype (Millner, L. M., Linder, M. W., and Valdes, R., Jr. 2013. Circulating tumor cells: a review of present methods and the need to identify heterogeneous phenotypes. *Annals of Clinical and Laboratory Science* 43:295-304). We have reproduced some of this data to establish the utility of our approach, including confirmation of epithelial marker E-Cadherin expression in HMLE cells and corresponding absence of mesenchymal protein marker Vimentin. HMLE-Twist1 cells display an inverse epithelial/mesenchymal expression profile to that of HMLE (FIG. 1A). In addition, HMLE-Twist1 cells are less sensitive to conventional chemotherapy relative to HMLE (FIG. 1B), a phenomenon ascribed to the cancer stem cell-like behavior of these EMT phenotypic cells.

Figure 2A:
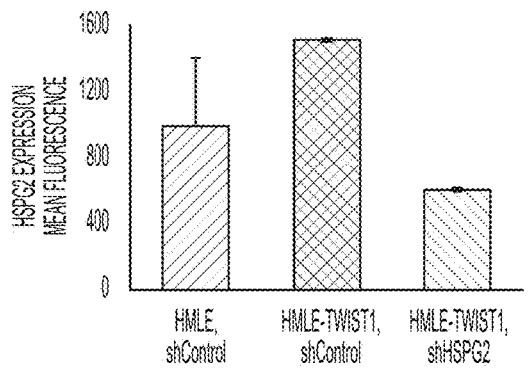
FIGS. 2A-2B. Confirmation of scFv binding partner HSPG2. (A) Lentiviral particles expressing either control shRNA or shRNA targeting HSPG2 were used to transduce HMLE and HMLE-Twist1 cells. Following stable selection in puromycin, cell surface HSPG2 expression was determined by flow cytometry using a commercial antibody recognizing a C-terminal epitope of HSPG2. Greater than 60% knockdown efficiency was observed compared to HMLE-Twist1 shControl cells. (B) Assessment of the relative binding of clone 6 scFv to HMLE-Twist1 cells after HSPG2 knockdown. Stable knock-down of HSPG2 reverts clone 6 scFv binding to the levels observed for HMLE control cells.
Figure 2B:
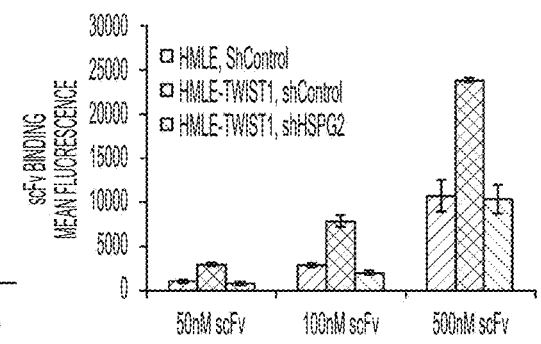

A two-color fluorescent scheme was employed to selectively sort HMLE-Twist1 target cells from mixed populations containing HMLE control cells, in the presence of phage library, via fluorescence activated cell sorting. Repeated iterations of this procedure yielded an scFv with selective affinity to EMT cells (data not shown). Using this approach, we were able to identify a candidate scFv ('clone 6') that can discriminate EM transitioned cells from controls. Biochemical pull-down experiments and subsequent mass spectrometry based protein identification identified the cell surface binding partner of clone 6 as Heparan Sulfate Proteoglycan 2 (HSPG2—data not shown). HSPG2 plays a role in metastasis via binding and sequestration of soluble growth factors, namely FGF-2, via Heparan Sulfate modifications. The growth factor sequestration function of HSPG2 has been shown to promote various aspects of malignancy, including invasiveness and angiogenesis (Millner, L. M., Linder, M. W., and Valdes, R., Jr. 2013. Circulating tumor cells: a review of present methods and the need to identify heterogeneous phenotypes. *Annals of Clinical and Laboratory Science* 43:295-304). We confirmed the target specificity of clone 6 by knockdown experiments. Approximately 60% stable knockdown of HSPG2 in HMLE-Twist1 cells was achieved via lentiviral transduction of shRNA (FIG. 2A, HMLE-Twist1 shControl vs. HMLE-Twist1 shHSPG2). HSPG2 knockdown reduced the ability of clone 6 scFv to bind HMLE-Twist1 cells, confirming the mass spectrometry based target identification approach (FIG. 2B).

Figures 3A, 3B:
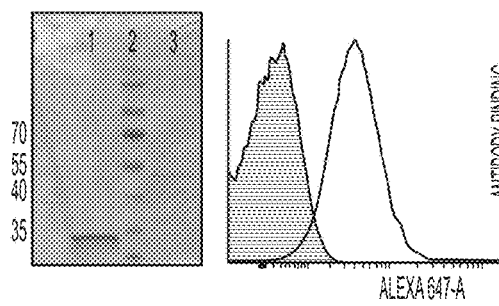
FIGS. 3A-3C. Diabody formation and assessment of binding to lung metastatic LM2 cells. (A) SDS-PAGE analysis of clone 6 scFv (lane 1—predicted MW 27 kDa), lane 2—MW ladder, lane 3—bivalent clone 6, which has a predicted MW Of 54 kDa. (B) Cell surface HSPG2 expression in MDA-MB-231 LM2 cells. Shaded histogram represents isotype control staining. Black histogram represents HSPG2 expression. (C) Relative LM2 cell surface binding of clone 6 scFv, diabody, and commercial IgG EpCAM antibodies, at equimolar concentration.

To establish the utility of clone 6 scFv in metastatic breast cancer models, we determined the expression of binding partner HSPG2, as well as the binding efficiency of clone 6 scFv, to the metastatic breast cancer cell line LM2. This cell line is an MDA-MB-231 clone that is derived from ex vivo expanded spontaneous lung metastases. LM2 cells are highly efficient at seeding lung metastasis in immunocompromised mice, and owing to co-expression of both Luciferase and GFP, can be used to both monitor metastatic colonization via non-invasive imaging, as well as CTC detection via flow cytometry (Aktas, B., Tewes, M., Fehm, T., Hauch, S., Kimmig, R., and Kasimir-Bauer, S. 2009. Stem cell and epithelial-mesenchymal transition markers are frequently overexpressed in circulating tumor cells of metastatic breast cancer patients. *Breast cancer research*: BCR 11:R46). HSPG2 expression was detected on the surface of LM2 cells (FIG. 3B). While clone 6 scFv demonstrated binding to LM2 cells, the binding affinity of clone 6 scFv was significantly lower when directly compared to equimolar concentrations of full length IgG Ep-CAM antibody. This phenomenon is a frequent observation for monovalent antibody fragments such as scFv relative to full length, bivalent IgG. As a result, it is desirable to engineer scFvs into multivalent molecules via shortening of the linker length between VH and VL of scFv. While the precise transition from scFv monomer to multimer is variable and unique to each scFv, it has been shown that reducing the scFv linker length from 15 amino acids to between 3-12 is sufficient to promote the formation of non-covalent scFv homo-dimers, termed diabodies (Kallergi, G., Papadaki, M. A., Politaki, E., Mavroudis, D., Georgoulias, V., and Agelaki, S. 2011. Epithelial to mesenchymal transition markers expressed in circulating tumour cells of early and metastatic breast cancer patients. *Breast cancer research*: BCR 13:R59). Diabodies are bivalent, dimeric scFvs that have been shown to display dramatic improvements in functional affinity and significantly slower dissociation rates to improve antigen binding and retention (Dean, M., Fojo, T., and Bates, S. 2005.

Figure 3C:
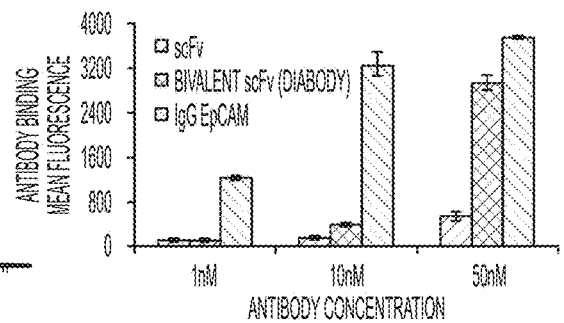

Tumour stem cells and drug resistance. *Nat Rev Cancer* 5:275-284; Trumpp, A., and Wiestler, O. D. 2008. Mechanisms of Disease: cancer stem cells—targeting the evil twin. *Nat Clin Pract Oncol* 5:337-347). We have generated a bivalent form of clone 6 scFv via linker scanning mutagenesis. An 8 amino acid linker was found to efficiently form an approx. 54 kDa homodimer (FIG. 3A). Bivalent scFv clone 6 displayed corn-parable binding to LM2 cells when compared to equimolar concentration to commercial IgG EpCAM antibody at 50 nM concentration (FIG. 3C).

Figure 4:
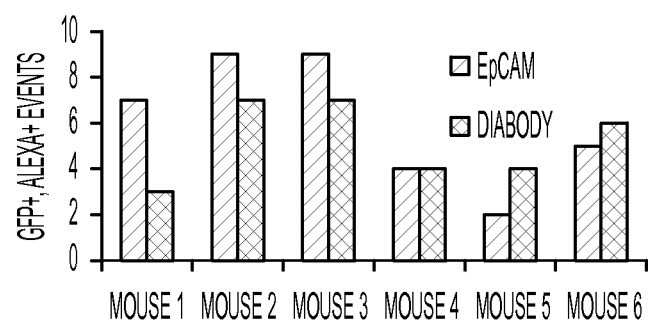
FIG. 4. LM2 cells were grafted orthotopically in Balb/c nude mice. Four weeks after tumor induction, mice were euthanized, and blood collected by cardiac puncture. Following erythrocyte lysis and CD45 magnetic depletion, the sample was divided into equal volumes, and labelling with 50 nM bivalent clone 6 or IgG EpCAM antibody, followed by Alexa647 secondary antibody was performed. The graph shows GFP/Alexa-647 double positive events for each animal are presented for both EpCAM and bivalent clone 6 labeling.
Figure 5A:
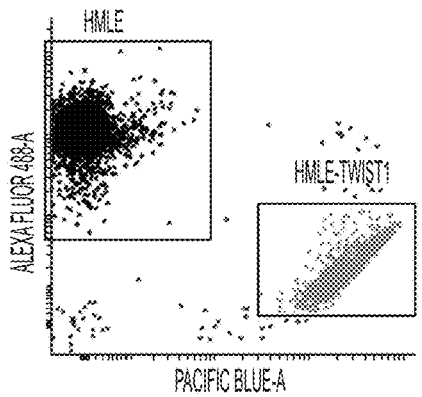
FIGS. 5A-5D. Phage display competitive cell panning data. (A) Representative dot plot of relative binding experiment. HMLE and HMLE-Twist1 cells are labelled with 10 μM of AF-488 and Pac Blue, respectively. Cells are labelled in separate tubes, washed, and mixed at a 1:1 ratio. 1E9 phage from sorted sub-libraries are added to the cell mixture and incubated with agitation for 30 min at 4° C. Cells are subsequently washed and labelled with an antibody recognizing the C-Myc tag of phage displaying scFv, followed by secondary Alexa-fluor 647 conjugate. (B) HMLE and HMLE-Twist1 are discriminated based on fluorescent labelling scheme in A. Each cell population is subsequently analyzed for C-myc AF 647 fluorescence intensity to determine relative binding of polyclonal phage sub-libraries (C) Graphical depiction of data in B. (D) Clone 6 scFv was identified as a selective binder to HMLE-Twist1 cells relative to HMLE.
Figure 5B:
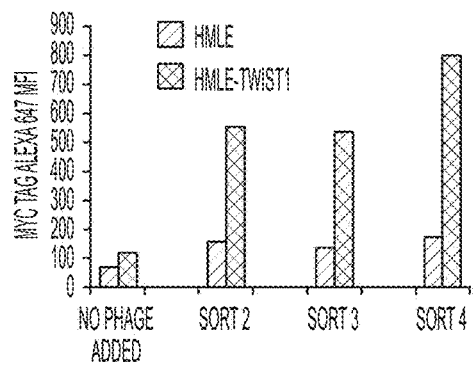
Figure 5C:
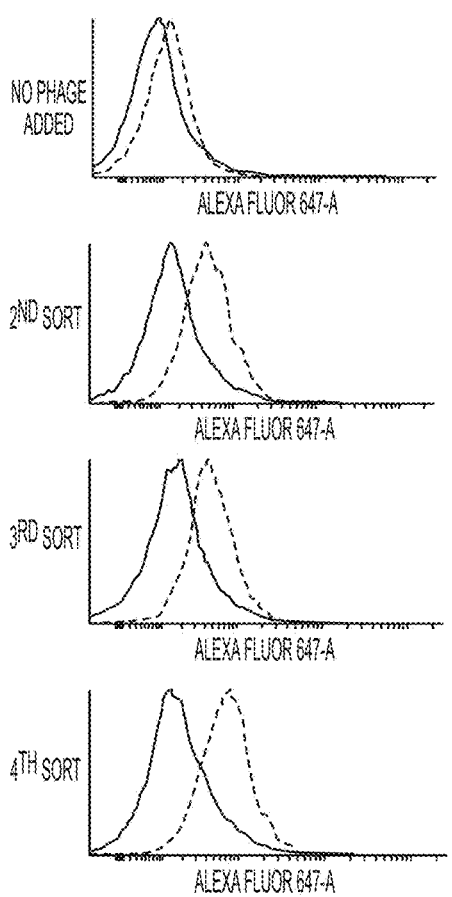
Figure 5D:
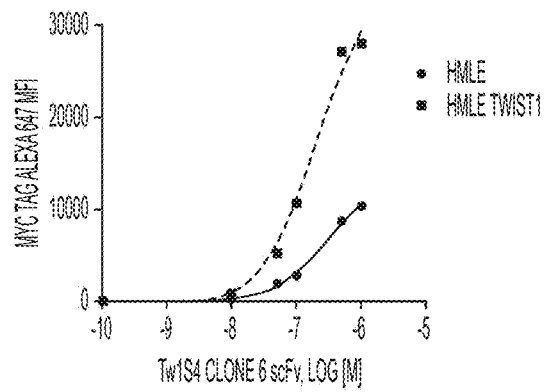
Figure 6A:
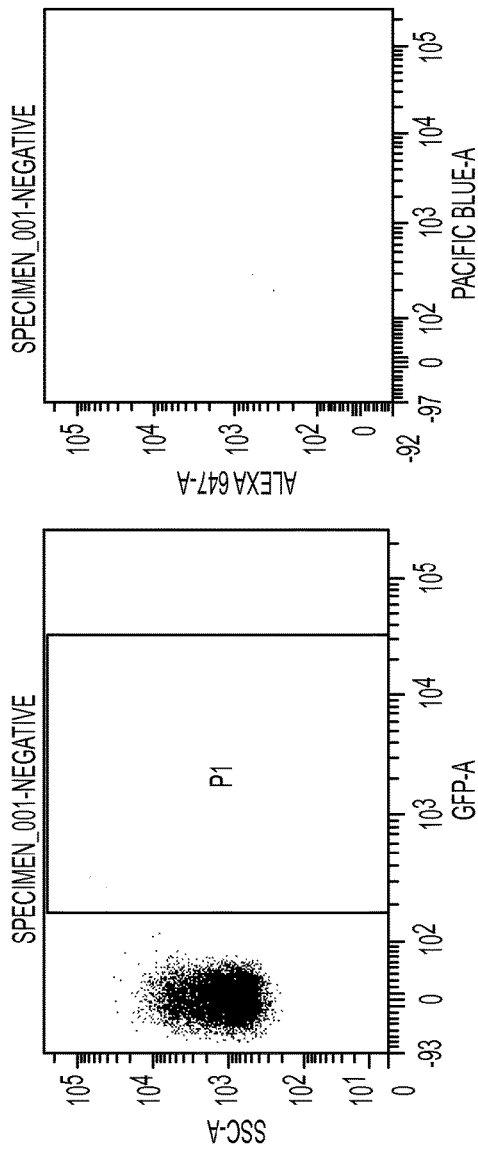
Figure 6B:
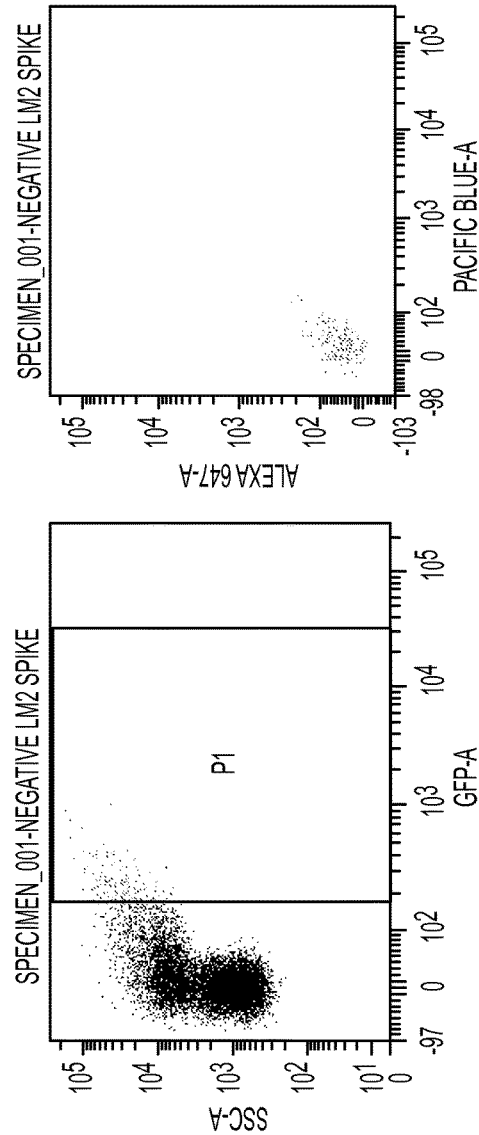

To best recapitulate the clinical scenario, LM2 cells were grafted orthotopically into mammary pad 9 of Balb/C nude mice. At 4 weeks, no detectable lung metastasis was observed via in vivo bioluminescence imaging (data not shown). We were, however, able to detect the presence of early stage metastatic dissemination via isolation of peripheral blood, which contained GFP+ CTCs derived from the primary tumor. After erythrocyte lysis and CD45+ cell depletion steps, the samples were separated into two equal fractions, and stained with 50 nM of bivalent clone 6 scFv or IgG EpCAM antibody. Fluorescence gating was established with non-tumor bearing mouse samples, to which LM2 cells were spiked in to establish GFP− from GFP+ events. Intra-sample comparison showed marked similarity in number of cells captures with anti-EpCAM antibody and bivalent clone 6 scFv (FIG. 4). Determination of EpCAM and HSPG2 expression levels on CTCs labeled by EpCAM antibody and bivalent clone 6 will provide critical information as to whether bivalent clone 6 is in fact identifying a distinct, mesenchymal CTC population.

In summary, we have developed an engineered antibody fragment that is capable of binding CTCs in an in vivo model of human metastatic breast cancer. Its target antigen, HSPG2, represents a potentially unique cell surface biomarker of mesenchymal CTCs. When used in conjunction with the conventional IgG EpCAM magnetic capture approach, we envision bivalent clone 6 as providing a complimentary approach to capture the full complement of CTCs to be enumerated.

EXAMPLE 2

An in vivo breast cancer metastasis model was employed to compare relative binding of EpCAM IgG and clone 6 diabody to CTCs.

Methods

The Tomlinson phage display library has on the order $10^9$ structurally distinct scFv displayed on the surface of bacteriophage, in monovalent format. Two fluorescent cell viability dyes, Calcein AM-450 and CFSE, were used to discriminate human mammary epithelial cells (HMLE), from a sub-population of HMLE cells stably expressing Twist1, a transcription factor known to induce EMT. HMLE cells were labeled with 10 μM CFSE at $10^6$ cells/mL and mixed at 100:1 ratio with Calcein AM-450 labelled HMLE-Twist1 cells. $10^9$ PFU naive phage library was added to the cell suspension. Following incubation, the target HMLE-Twist1 cells are sorted from the mixed population using a BD FACS Aria cell sorter. Phage bound to target cells are eluted in pH 2 glycine buffer, and propagated to generate sub-libraries. Sub-libraries, designated Tw1_S1 through Tw1_S4, represent polyclonal populations of recovered phage from target cells After 4 competitive enrichment experiments performed in series, the original library diversity of $10^9$ is thus sequentially narrowed to a manageable population of candidate clones displaying selective binding to HMLE-Twist1 cells. Clone 6 displays selective binding to HMLE-Twist1, and was engineered to bivalent homodimer via linker scanning mutagenesis. Subsequent analysis of binding characteristics of clone 6 diabody was performed.

Results and Discussion

To accomplish our goal of identifying an antibody suitable for immunocapture of mesenchymal CTCs, we have developed an in vitro competition based bio-panning procedure. An isogenic matched mammary epithelial cell line pair was employed (HMLE—control mammary epithelial cells, and HMLE-Twist1, an EMT phenotypic cell line). These cells have been previously characterized in a seminal paper demonstrating that EMT is accompanied by acquisition of a highly aggressive phenotype. Biochemical pull-down experiments and subsequent mass spectrometry based protein identification identified the cell surface binding partner of clone 6. 60% stable knockdown of the target receptor in HMLE-Twist1 cells was achieved via lentiviral transduction of shRNA. Target receptor knockdown reduced the ability of clone 6 scFv to bind HMLE-Twist1 cells (FIGS. 5A-5D).

To establish the utility of clone 6 scFv in metastatic breast cancer models, we determined the expression of binding partner, as well as the binding efficiency of clone 6 scFv, to the metastatic breast cancer cell line LM2. LM2 cells were grafted orthotopically to mammary pad 9 of BALB/C nude mice. At 4 weeks, no detectable lung metastasis was observed via in vivo bioluminescence imaging (data not shown). We were able to detect the presence of early stage metastatic dissemination via isolation of peripheral blood, which contained GFP+ CTCs derived from the primary tumor. Fluorescence gating was established with non-tumor bearing mouse samples, to which LM2 cells were spiked in, to establish GFP− from GFP+ events. Intra-sample comparison showed bivalent clone 6 is identifying a distinct, mesenchymal CTC population (FIGS. 6A-6E).

Conclusion

Clone 6 diabody is capable of binding CTCs in an in vivo model of metastatic breast cancer. The target antigen represents a potentially unique cell surface biomarker of mesenchymal CTCs. When used in conjunction with the conventional IgG EpCAM magnetic capture, we envision bivalent clone 6 as providing a highly complementary approach to capture of mesenchymal CTCs, enabling the full suite of CTCs to be enumerated.

EXAMPLE 3

To further improve the binding affinity, we engineered a full length IgG (Tw1S4_6 IgG) that showed high affinity for various metastatic cell lines (FIG. 8, top panel) and showed greater binding to HMLE-Twist1, an EMT phenotypic cell line relative to HMLE, control mammary epithelial cells (FIG. 8, bottom panel).

Figure 9A:
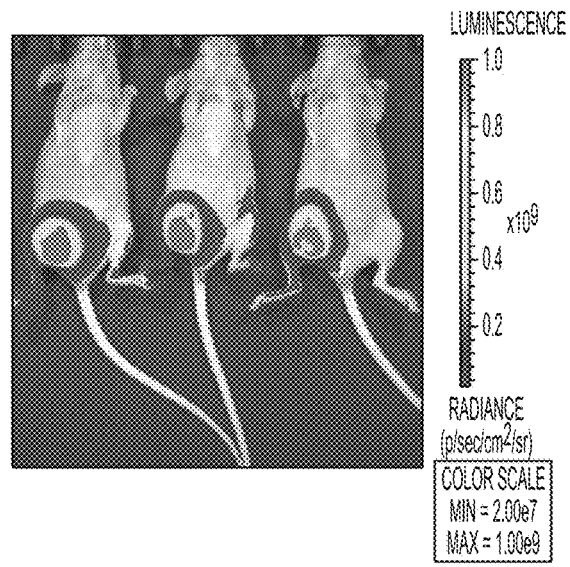
FIGS. 9A-9C. In vivo circulating tumor cell model. LM2 cells are grafted orthotopically to the right flank mammary pad ($5*10^6$ cells/mouse) in the presence of matrigel. Following 6 weeks of orthotopic tumor growth, animals are sacrificed and whole peripheral blood is collected into EDTA vacutubes via cardiac puncture. Panel A presents luminescence signal to confirm orthotopic tumor growth. Density gradient centrifugation over Ficoll paque is used to isolate mononuclear cells from whole peripheral blood, which includes potential circulating tumor cells. Following RBC lysis, cells are stained with CD45-PE labelled antibodies targeting mouse leukocyte, Pac blue labelled human EpCAM IgG, and Dylight 647 labelled Tw1S4_6 IgG. (B) Fluorescence activated cell sorting was employed to capture Tw1S4_6 and EpCAM labelled CTCs separately. CD45 counterstain is used to confirm that sorted cells are not of murine origin (area P7 on figure B). (C) Within the CD45 negative P7 population shown in panel B, events staining positive for either Tw1S4_6 IgG (area P5) or EpCAM (area P1).
Figure 9B:
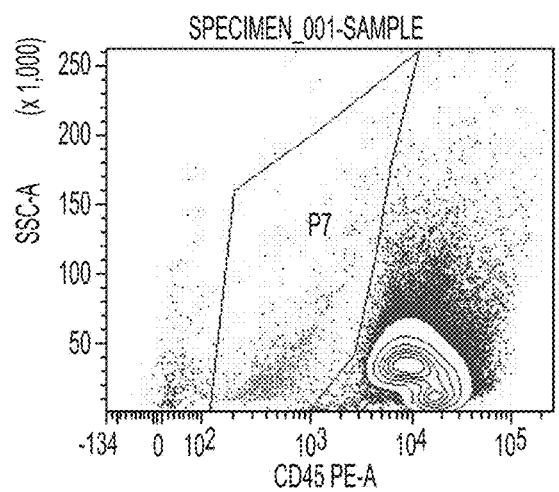
Figure 9C:
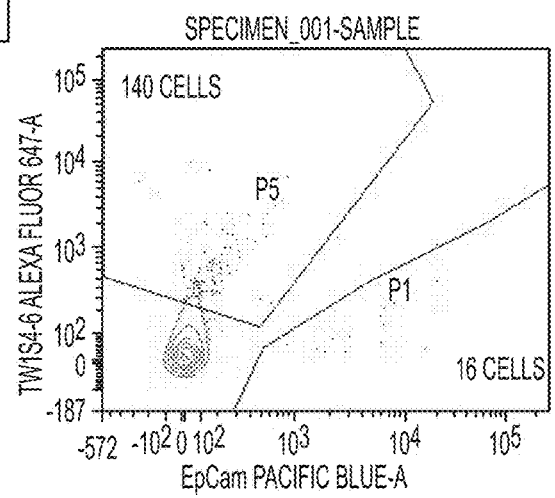

The antibody heavy and light chain sequences with the variable regions, that are derived from the original scFv, highlighted in bold, and the translated protein sequence for each of the variable regions (FIGS. 16A-16C). These sequences are contained in the full length antibody (human IgG1). Two copies of each, heavy and light chain, comprise the full antibody, which has an approximate molecular weight of 150,000 daltons. The remaining DNA sequence is from the vector backbone that encodes for the constant region of the heavy and light chain respectively. The ability of Tw1S4_6 IgG to selectively identify circulating tumor cells was evaluated in vivo. MDA-MB-231-LM2 cells were grafted into mammary pad of Balb/C nude mice. At 6 weeks, no detectable metastasis was observed via bioluminescence imaging (FIG. 9A). We were, however, able to detect the presence of early stage metastatic dissemination via isolation of peripheral blood, which contained GFP+ CTCs derived from the primary tumor. After erythrocyte lysis, the samples were separated into two equal fractions, and stained with 50 nM of Tw1S4_6 IgG or anti-EpCAM antibody. Fluorescence gating was established with non-tumor bearing mouse samples, to which the GFP+ LM2 cells were spiked in. CD45 counterstaining was used to exclude the leukocyte population (FIG. 9B). Intra-sample comparison showed distinct cell populations captured with anti-EpCAM antibody and Tw1S4_6 IgG (FIG. 9C).

Figure 10:
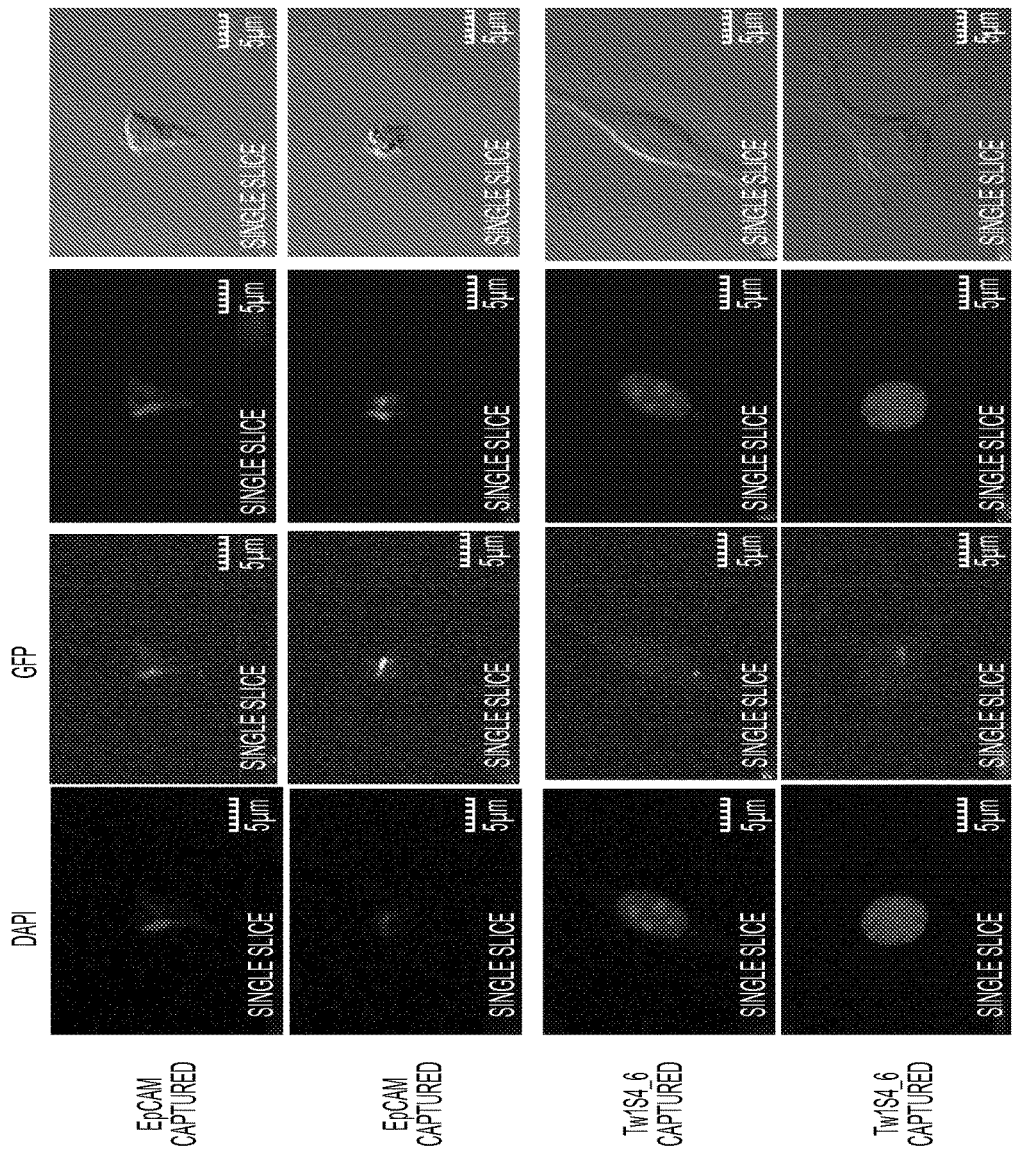
FIG. 10. Immunofluorescence staining of sorted circulating tumor cells. Cells captured by EpCAM IgG (top two panels) or Tw1S4_6 IgG bottom two panels) were assayed for EpCAM expression using commercial PE-EpCAM IgG antibody. Nuclear counterstaining was performed with DAPI. Images were acquired on an Olympus fluoview FV1000 upright confocal microscope under 40× oil immersion objective.
Figure 11:
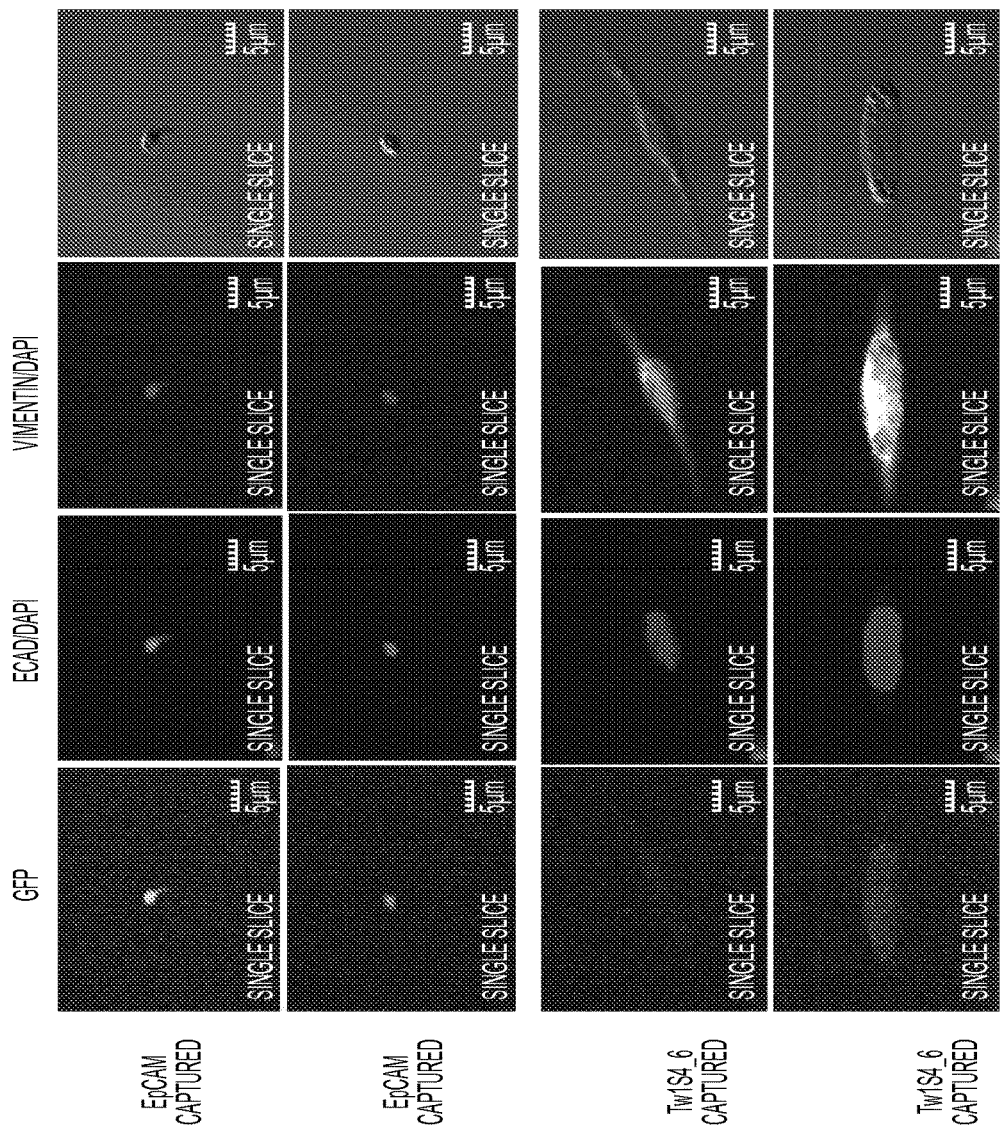
FIG. 11. Immunofluorescence staining of sorted circulating tumor cells. Cells captured by EpCAM IgG (top two panels) or Tw1S4_6 IgG bottom two panels) were assayed for EMT marker protein expression using commercial PE-E-Cadherin IgG, and Dylight 650 Vimentin IgG antibodies. Nuclear counterstaining was performed with DAPI. Images were acquired on an Olympus fluoview FV1000 upright confocal microscope under 40× oil immersion objective.

The cells captured by Tw1S4_6 IgG were negative for EpCAM expression whereas cells captured by anti-EpCAM antibody was positive for EpCAM expression (FIG. 10). Further, cells captured by Tw1S4_6 IgG stained positive for mesenchymal marker vimentin and negative for epithelial marker E-cadherin while cells captured by the anti-EpCAM antibody stained negative for mesenchymal marker vimentin and positive for epithelial marker E-cadherin (FIG. 11).

Figure 12:
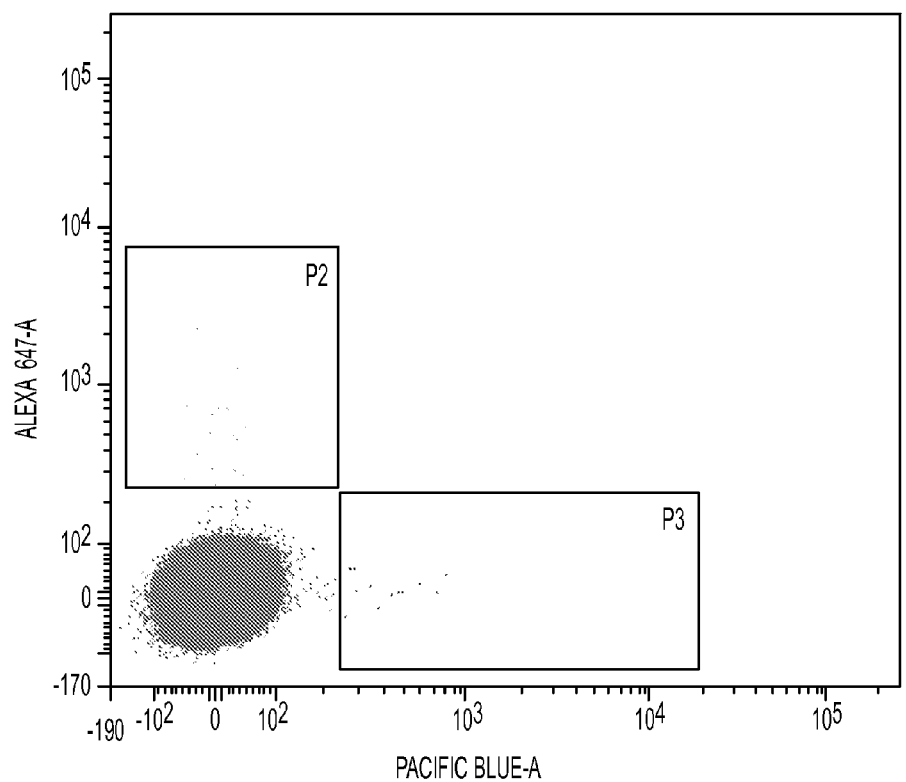
FIG. 12. CTC detection in a Patient Derived xenograft (PDX) melanoma model (M12). Whole blood from tumor-bearing mice was collected in anti-coagulant tubes and was fractionated via ficoll paque density gradient. Following RBC lysis, peripheral blood mononuclear cells contained in the buffy coat were stained with 50 nM of Alexa 647 labelled Tw1S4_6 IgG and Pacific blue labelled EpCAM IgG, along with mouse Fc block reagent. Distinct populations can be observed (populations P2—Tw1S4_6 and P3—EpCAM), indicating that the Tw1S4_6 IgG is identifying a distinct population of circulating tumor cells.
Figure 13:
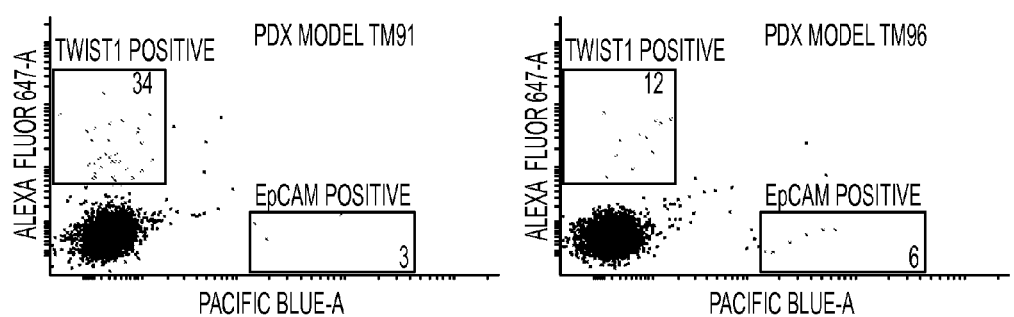
FIG. 13. CTC detection in a Patient Derived xenograft (PDX) breast cancer models. Whole blood from tumor-bearing mice was collected in anti-coagulant tubes and was fractionated via ficoll paque density gradient. Following RBC lysis, peripheral blood mononuclear cells contained in the buffy coat were stained with 50 nM of Alexa 647 labelled Tw1S4 IgG and Pacific blue labelled EpCAM IgG, along with mouse Fc block reagent. Distinct populations can be observed, indicating that the Tw1S4_6 IgG is identifying a distinct population of circulating tumor cells in each of the two models studied (TM91 and TM96).

We then extended these studies to PDX models of triple-negative breast cancer (TM91 and TM96; Jackson Labs) and melanoma (M12; provided by Dr. Jann Sarkaria, Mayo Clinic, Rochester, Minn.). Similar to that seen with the MDA-MB-231-LM2 tumor model, distinct cell populations were captured with anti-EpCAM and Clone 6 antibodies in both the melanoma (FIG. 12) and breast cancer models (FIG. 13).

Figure 14A:
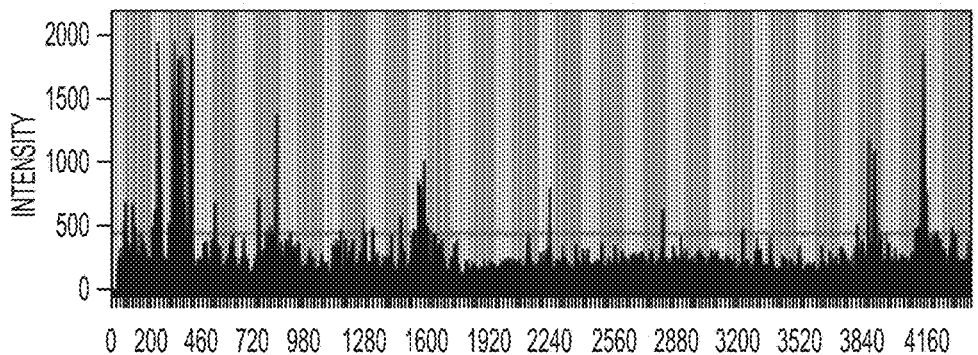
FIGS. 14A-14E. (A) Epitope mapping for Tw1S4_6 IgG. The epitope mapping strategy used linear HSPG2 amino acid sequence in 20 mer peptide fragments, each having an overlap of 16 amino acids. Tw1S4_6 binding site was identified in high-throughput ELISA format. Tw1S4_6 binding was observed above background levels throughout linearized HSPG2, indicating that the epitope recognized by Tw1S4_6 is likely discontinuous. Several pockets of concentrated binding were observed at N-terminal residues <500, and C-terminal residues >3800. These regions roughly correspond to the first and fifth domains of HSPG2 (B) ELISA showing Tw1S4_6 IgG binds to HSPG2 domain 1. (C) Tw1S4_6 IgG binding titration curve for binding to MDA-MB-231-LM2 determined using flow cytometry (D) ELISA demonstrating Tw1S4_6 IgG selectively binds HSPG2 domain 1 relative to domain 5. (E) Competitive inhibition of Tw1 S4_6 IgG binding to LM2 cells with increasing soluble HSPG2 domain 1 peptide.

We also mapped the binding epitope of Tw1S4_6 IgG on HSPG2 (Perlecan) using a custom peptide array platform (CLIPS; Pepscan). The CLIPS technology structurally fixes peptides into defined three-dimensional structures. This results in functional mimics of even the most complex binding sites. CLIPS library screening starts with the conversion of the target protein into a library of overlapping peptide constructs, using a combinatorial matrix design. On a solid carrier, a matrix of linear peptides is synthesized, which are subsequently shaped into spatially defined CLIPS constructs. Constructs representing both parts of the discontinuous epitope in the correct conformation bind the antibody with high affinity. Constructs presenting the incomplete epitope bind the antibody with lower affinity, whereas constructs not containing the epitope do not bind at all. Affinity information is used in iterative screens to define the sequence and conformation of epitopes in detail. This study suggested that Domain 1 and possibly Domain 5 represent the binding epitope(s) for Tw1S4_6 IgG (FIG. 14A).

Figure 14B:
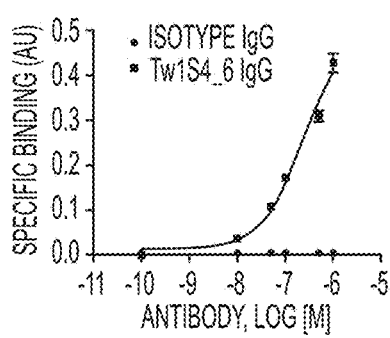
Figure 14C:
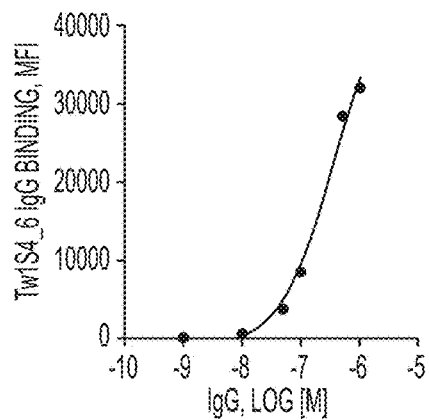
Figure 14D:
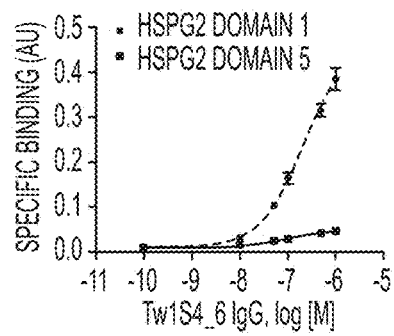
Figure 14E:
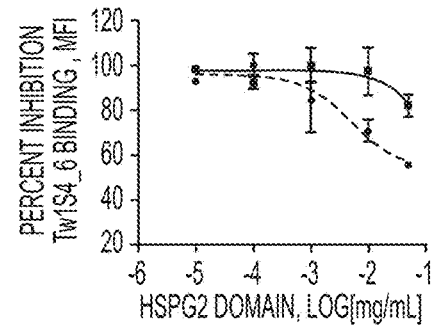

ELISA-based studies utilizing a soluble form of the truncated domain 1 protein showed that Tw1S4_6 IgG binds in a concentration-dependent fashion and with high affinity to HSPG2 domain 1 (FIG. 14B). ELISA studies utilizing soluble forms of the truncated domain 1 and 5 proteins further demonstrated that Tw1S4_6 IgG selectively binds HSPG2 domain 1 relative to domain 5 (FIG. 14D). Flow cytometry studies showed that a soluble form of the truncated domain 1 protein, but not a soluble form of the truncated domain 5 protein, competitively inhibited the binding of Tw1S4_6 IgG to LM2 cells. The binding curve of Tw1S4_6 IgG to LM2 cells in the absence of any competition is shown in FIG. 14C. These studies strongly point to domain 1 of HSPG2 as the binding epitope of Tw1S4_6 IgG.

EXAMPLE 4

Metastasis is responsible for over 90% of cancer-related deaths. There is an urgent need for therapies directed specifically towards metastasis. We have developed a human IgG (Tw1S4_6 IgG) that targets circulating tumor cells. The antibody was derived from a cell panning procedure using scFv phage display. It was subsequently reformatted to a fully human IgG. The aim of this study was to synthesize PEGlylated poly(lactide-co-glycolide) (PLGA) nanoparticles (NPs) conjugated to Tw1S4_6 IgG and carry out in vitro studies to test this formulation against metastatic tumor cells.

Coumarin-6 (fluorescent dye used to label nanoparticles) loaded PLGA NPs were synthesized by single emulsion solvent evaporation. They were surface functionalized with poly(lactic acid) (PLA)—polyethylene glycol (PEG)—Maleimide (Mal). The antibodies were thiolated using 2-iminothiolane followed by conjugation to NPs via Thiol-Maleimide chemistry. Post-conjugation, the NPs were washed and lyophilized. As shown in FIG. 15A, Tw1S4_6 IgG-functionalized NPs had significantly higher uptake in the metastatic cell line. Further, a greater fraction of the internalized Tw1S4_6 IgG-functionalized NPs was retained within the cells (FIG. 15B). This study shows that Tw1S4_6 IgG is able to provide targeting properties to drug carriers such as nanoparticles.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An immune reagent comprising a first scFv antibody fragment that specifically binds to membrane protein HSPG2 (Perlecan), wherein the first scFv antibody fragment is Clone-6 (SEQ ID NO:2).

2. The immune reagent of claim 1, wherein the immune reagent is about 26-29 kDa.

3. The immune reagent of claim 1, further comprising a second scFv antibody fragment operably linked to the first scFv antibody fragment to form a diabody.

4. The immune reagent of claim 3, wherein both the first and second scFv antibody fragments are Clone-6 (SEQ ID NO:2).

5. The immune reagent of claim 3, wherein the first and second antibody fragments are linked by means of a linker.

6. The immune reagent of claim 3, further comprising a poly-His tail operably linked to either the first or second antibody fragment.

7. An immune reagent comprising
   (a) a heavy chain encoded by a nucleic acid having 100% identity to SEQ ID NO:3 and a light chain encoded by a nucleic acid having 100% identity to SEQ ID NO:5; or
   (b) a heavy chain variable region having 100% identity to SEQ ID NO:4 and a light chain variable region having 100% identity to SEQ ID NO:6.

8. An immunoglobulin comprising a first immune reagent of claim 7 operably linked to a second immune reagent of claim 7.

9. A conjugate comprising the immune reagent of claim 1 conjugated to a detection agent and/or therapeutic agent.

10. The conjugate of claim 9, wherein the detection agent or therapeutic agent comprises a radionuclide.

11. The conjugate of claim 10, wherein the radionuclide is selected from Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

12. The conjugate of claim 9, wherein the immune reagent is conjugated to a detection agent.

13. The conjugate of claim 12, wherein the detection agent comprises a fluorescent group.

14. The conjugate of claim 13, wherein the fluorescent group is fluorescein, tetrachlorofluorescein, hexachlorofluorescein, tetramethylrhodamine, rhodamine, cyanine-derivative dyes, Texas Red, Bodipy, and/or Alexa dye.

15. The conjugate of claim 9, wherein the immune reagent is conjugated to a therapeutic agent.

16. The conjugate of claim 15, wherein the therapeutic agent is a cytotoxic compound.

17. The conjugate of claim 16, wherein the cytotoxic compound is a chemotherapeutic agent.

18. The conjugate of claim 17, wherein the chemotherapeutic agent is selected from all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib and/or Vandetanib.

19. A pharmaceutical composition comprising the immune reagent of claim 1 and a pharmaceutically acceptable excipient.

20. A composition comprising an immune agent of claim 1 operably linked to a carrier.

21. The composition of claim 20 wherein the carrier is a nanoparticle or liposome.

22. A method of inhibiting proliferation and/or growth of a tumor by administering the immune reagent of claim 1 to a patient in need thereof.

23. A method of inhibiting proliferation and/or growth of a tumor by administering the immune reagent of claim 7 to a patient in need thereof.

24. A method of inhibiting proliferation and/or growth of a tumor by administering the conjugate of claim 9 to a patient in need thereof.

* * * * *

SEQUENCE LISTING

<160> NUMBER OF SEQ ID NOS: 7

<210> SEQ ID NO 1
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
aaggagacag tcataatgaa atacctattg cctacggcag ccgctggatt gttattactc      60
gcggcccagc cggccatggc cgaggtgcag ctgttggagt ctggggagg cttggtacag     120
cctgggggt ccctgagact ctcctgtgca gcctctggat tcacctttag cagctatgcc     180
atgagctggg tccgccaggc tccagggaag gggctggagt gggtctcagc gattagggag     240
gatggtatta agacatatta cgcagactcc gtgaagggcc ggttcaccat ctccagagac     300
aattccaaga acacgctgta tctgcaaatg aacagcctga gagccgagga cacggccgta     360
tattactgtg cgaaaagggc tcgtcggttt gactactggg gccagggaac cctggtcacc     420
gtctcgagcg gtggaggcgg ttcaggcgga ggtggcagcg gcggtggcgg gtcgacggac     480
atccagatga cccagtctcc atcctccctg tctgcatctg taggagacag agtcaccatc     540
acttgccggg caagtcagag cattagcagc tatttaaatt ggtatcagca gaaaccaggg     600
aaagcccctaa gctcctgat ctataatgca tccctttttgc aaagtggggt cccatcaagg     660
ttcagtggca gtggatctgg gacagatttc actctcacca tcagcagtct gcaacctgaa     720
gattttgcaa cttactactg tcaacagagt ctgcgttcgc ctattacgtt cggccaaggg     780
accaaggtgg aaatcaaacg ggcggccgca catcatcatc accatcac                  828
```

<210> SEQ ID NO 2
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
                20                  25                  30

Leu Val Gln Pro Gly Gly Ser Leu Arg Leu Ser Cys Ala Ala Ser Gly
            35                  40                  45

Phe Thr Phe Ser Ser Tyr Ala Met Ser Trp Val Arg Gln Ala Pro Gly
        50                  55                  60

Lys Gly Leu Glu Trp Val Ser Ala Ile Arg Glu Asp Gly Ile Lys Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Arg Ala Arg Arg Phe Asp Tyr Trp
        115                 120                 125

Gly Gln Gly Thr Leu Val Thr Val Ser Ser Gly Gly Gly Gly Ser Gly
    130                 135                 140
```

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Asn Ala Ser Leu Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Leu Arg Ser Pro Ile Thr Phe Gly Gln Gly Thr
                245                 250                 255

Lys Val Glu Ile Lys Arg Ala Ala Ala His His His His His His
            260                 265                 270

```
<210> SEQ ID NO 3
<211> LENGTH: 4258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgtacagga tgcaactcct gtcttgcatt gcactaagtc ttgcacttgt cacgaattcg      60
gaggtgcagc tgttggagtc tgggggaggc ttggtacagc ctggggggtc cctgagactc     120
tcctgtgcag cctctggatt cacctttagc agctatgcca tgagctgggt ccgccaggct     180
ccagggaagg ggctggagtg ggtctcagcg attagggagg atggtattaa acatatattac    240 gcagactccg tgaagggccg gttcaccatc tccagagaca attccaagaa cacgctgtat     300
ctgcaaatga acagcctgag agccgaggac acggccgtat attactgtgc gaaagggct     360 cgtcggtttg actactgggg ccagggaacc ctggtcaccg tctcgagcgc tagcaccaag     420
ggcccatcgg tcttccccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
```

-continued

```
gtcttctcat gctccgtgat gcatgaggct ctgcacaacc actacacgca aagagcctc      1380
tccctgtctc cgggtaaatg agtcctagct ggccagacat gataagatac attgatgagt      1440
ttggacaaac cacaactaga atgcagtgaa aaaaatgctt tatttgtgaa atttgtgatg      1500
ctattgcttt atttgtaacc attataagct gcaataaaca agttaacaac aacaattgca      1560
ttcattttat gtttcaggtt caggggagg tgtgggaggt tttttaaagc aagtaaaacc      1620
tctacaaatg tggtatggaa ttaattctaa aatacagcat agcaaaactt taacctccaa      1680
atcaagcctc tacttgaatc cttttctgag ggatgaataa ggcataggca tcagggctg       1740
ttgccaatgt gcattagctg tttgcagcct caccttcttt catggagttt aagatatagt      1800
gtattttccc aaggtttgaa ctagctcttc atttctttat gttttaaatg cactgacctc      1860
ccacattccc tttttagtaa aatattcaga ataatttaa atacatcatt gcaatgaaaa       1920
taaatgtttt ttattaggca gaatccagat gctcaaggcc cttcataata tcccccagtt     1980
tagtagttgg acttagggaa caaaggaacc tttaatagaa attggacagc aagaaagcga      2040
gcttctagct tatcctcagt cctgctcctc tgccacaaag tgcacgcagt tgccggccgg      2100
gtcgcgcagg gcgaactccc gcccccacgg ctgctcgccg atctcggtca tggccggccc     2160
ggaggcgtcc cggaagttcg tggacacgac ctccgaccac tcggcgtaca gctcgtccag     2220
gccgcgcacc cacacccagg ccagggtgtt gtccggcacc acctggtcct ggaccgcgct     2280
gatgaacagg gtcacgtcgt cccggaccac accggcgaag tcgtcctcca cgaagtcccg     2340
ggagaacccg agccggtcgg tccagaactc gaccgctccg gcgacgtcgc gcgcggtgag     2400
caccggaacg gcactggtca acttggccat gatggctcct cctgtcagga gaggaaagag     2460
aagaaggtta gtacaattgc tatagtgagt tgtattatac tatgcagata tactatgcca      2520
atgattaatt gtcaaactag ggctgcaggg ttcatagtgc cacttttcct gcactgcccc     2580
atctcctgcc cacccttcc caggcataga cagtcagtga cttaccaaac tcacaggagg       2640
gagaaggcag aagcttgaga cagacccgcg ggaccgccga actgcgaggg gacgtggcta     2700
gggcggcttc ttttatggtg cgccggccct cggaggcagg gcgctcgggg aggcctagcg     2760
gccaatctgc ggtggcagga ggcggggccg aaggccgtgc ctgaccaatc cggagcacat     2820
aggagtctca gcccccgcc ccaaagcaag gggaagtcac gcgcctgtag cgccagcgtg      2880
ttgtgaaatg ggggcttggg ggggttgggg ccctgactag tcaaaacaaa ctcccattga     2940
cgtcaatggg gtggagactt ggaaatcccc gtgagtcaaa ccgctatcca cgcccattga     3000
tgtactgcca aaccgcatc atcatggtaa tagcgatgac taatacgtag atgtactgcc      3060
aagtaggaaa gtcccataag gtcatgtact gggcataatg ccaggcgggc catttaccgt     3120
cattgacgtc aataggggc gtacttggca tatgatacac ttgatgtact gccaagtggg      3180
cagtttaccg taaatactcc acccattgac gtcaatggaa agtccctatt ggcgttacta     3240
tgggaacata cgtcattatt gacgtcaatg ggcggggtc gttgggcggt cagccaggcg      3300
ggccatttac cgtaagttat gtaacgcctg caggttaatt aagaacatgt gagcaaaagg     3360
ccagcaaaag gccaggaacc gtaaaaaggc cgcgttgctg gcgttttcc ataggctccg       3420
cccccctgac gagcatcaca aaaatcgacg ctcaagtcag aggtggcgaa acccgacagg     3480
actataaaga taccaggcgt ttccccctgg aagctccctc gtgcgctctc ctgttccgac     3540
cctgccgctt accggatacc tgtccgcctt tctcccttcg ggaagcgtgg cgctttctca     3600
tagctcacgc tgtaggtatc tcagttcggt gtaggtcgtt cgctccaagc tgggctgtgt     3660
gcacgaaccc cccgttcagc ccgaccgctg cgccttatcc ggtaactatc gtcttgagtc     3720
```

```
caacccggta agacacgact tatcgccact ggcagcagcc actggtaaca ggattagcag    3780
agcgaggtat gtaggcggtg ctacagagtt cttgaagtgg tggcctaact acggctacac    3840
tagaagaaca gtatttggta tctgcgctct gctgaagcca gttaccttcg aaaaagagt     3900 tggtagctct tgatccggca acaaaccac cgctggtagc ggtggttttt ttgtttgcaa     3960
gcagcagatt acgcgcagaa aaaaggatc tcaagaagat cctttgatct tttctacggg    4020
gtctgacgct cagtggaacg aaaactcacg ttaagggatt ttggtcatgg ctagttaatt    4080
aacatttaaa tcagcggccg caataaaata tctttatttt cattacatct gtgtgttggt    4140
tttttgtgtg aatcgtaact aacatacgct ctccatcaaa acaaaacgaa acaaaacaaa    4200
ctagcaaaat aggctgtccc cagtgcaagt gcaggtgcca gaacatttct ctatcgaa     4258

<210> SEQ ID NO 4
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Arg Glu Asp Gly Ile Lys Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Arg Ala Arg Arg Phe Asp Tyr Trp
        115                 120                 125

Gly Gln Gly Thr Leu Val Thr Val Ser
    130                 135

<210> SEQ ID NO 5
<211> LENGTH: 3623
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgtacagga tgcaactcct gtcttgcatt gcactaagtc ttgcacttgt cacgaattca     60
acggacatcc agatgaccca gtctccatcc tccctgtctg catctgtagg agacagagtc    120
accatcactt gccgggcaag tcagagcatt agcagctatt taaattggta tcagcagaaa    180
ccagggaaag cccctaagct cctgatctat aatgcatccc ttttgcaaag tggggtccca    240
tcaaggttca gtggcagtgg atctgggaca gatttcactc tcaccatcag cagtctgcaa    300
cctgaagatt ttgcaactta ctactgtcaa cagagtctgc gttcgcctat tacgttcggc    360
```

```
caagggacca aggtggaaat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag acagcacct acagcctcag cagcaccctg     600
acgctgagca agcagacta cgagaaacac aaagtctacg cctgcgaagt cacccatcag     660
ggcctgagct cgcccgtcac aaagagcttc aacaggggag agtgttagag ggagctagct    720
cgacatgata agatacattg atgagtttgg acaaaccaca actagaatgc agtgaaaaaa    780
atgctttatt tgtgaaattt gtgatgctat tgctttattt gtgaaatttg tgatgctatt    840
gctttatttg taaccattat aagctgcaat aaacaagtta acaacaacaa ttgcattcat    900
tttatgtttc aggttcaggg ggaggtgtgg gaggttttt aaagcaagta aaacctctac     960
aaatgtggta tggaattaat tctaaaatac agcatagcaa aactttaacc tccaaatcaa   1020
gcctctactt gaatccttt ctgagggatg aataaggcat aggcatcagg ggctgttgcc    1080
aatgtgcatt agctgtttgc agcctcacct tctttcatgg agtttaagat atagtgtatt   1140
ttcccaaggt ttgaactagc tcttcatttc tttatgtttt aaatgcactg acctcccaca   1200
ttcccttttt agtaaaatat tcagaaataa tttaaataca tcattgcaat gaaaataaat   1260
gttttttatt aggcagaatc cagatgctca aggcccttca taatatcccc cagtttagta   1320
gttggactta gggaacaaag gaacctttaa tagaaattgg acagcaagaa agcgagcttc   1380
tagctttagt tcctggtgta cttgaggggg atgagttcct caatggtggt tttgaccagc   1440
ttgccattca tctcaatgag cacaaagcag tcaggagcat agtcagagat gagctctctg   1500
cacatgccac aggggctgac caccctgatg gatctgtcca cctcatcaga gtaggggtgc   1560
ctgacagcca caatggtgtc aaagtccttc tgcccgttgc tcacagcaga cccaatggca   1620
atggcttcag cacagacagt gaccctgcca atgtaggcct caatgtggac agcagagatg   1680
atctccccag tcttggtcct gatggccgcc ccgacatggt gcttgttgtc ctcatagagc   1740
atggtgatct tctcagtggc gacctccacc agctccagat cctgctgaga gatgttgaag   1800
gtcttcatga tggctcctcc tgtcaggaga ggaaagagaa gaaggttagt acaattgcta   1860
tagtgagttg tattatacta tgcttatgat taattgtcaa actagggctg cagggttcat   1920
agtgccactt ttcctgcact gccccatctc ctgcccaccc tttcccaggc atagacagtc   1980
agtgacttac caaactcaca ggagggagaa ggcagaagct tgagacagac ccgcgggacc   2040
gccgaactgc gaggggacgt ggctagggcg gcttctttta tggtgcgccg gccctcggag   2100
gcagggcgct cggggaggcc tagcggccaa tctgcggtgg caggaggcgg ggccgaaggc   2160
cgtgcctgac caatccggag cacataggag tctcagcccc ccgccccaaa gcaagggaa    2220 gtcacgcgcc tgtagcgcca gcgtgttgtg aaatgggggc ttggggggt tggggccctg    2280 actagtcaaa acaaactccc attgacgtca atggggtgga gacttggaaa tccccgtgag   2340
tcaaaccgct atccacgccc attgatgtac tgccaaaacc gcatcatcat ggtaatagcg   2400
atgactaata cgtagatgta ctgccaagta ggaaagtccc ataaggtcat gtactgggca   2460
taatgccagg cgggccattt accgtcattg acgtcaatag gggcgtact tggcatatga    2520 tacacttgat gtactgccaa gtgggcagtt taccgtaaat actccaccca ttgacgtcaa   2580
tggaaagtcc ctattggcgt tactatggga acatacgtca ttattgacgt caatgggcgg   2640
gggtcgttgg gcggtcagcc aggcgggcca tttaccgtaa gttatgtaac gcctgcaggt   2700
```

```
taattaagaa catgtgagca aaaggccagc aaaaggccag gaaccgtaaa aaggccgcgt    2760
tgctggcgtt tttccatagg ctccgccccc ctgacgagca tcacaaaaat cgacgctcaa    2820
gtcagaggtg gcgaaacccg acaggactat aaagatacca ggcgtttccc cctggaagct    2880
ccctcgtgcg ctctcctgtt ccgaccctgc cgcttaccgg atacctgtcc gcctttctcc    2940
cttcgggaag cgtggcgctt tctcatagct cacgctgtag gtatctcagt tcggtgtagg    3000
tcgttcgctc caagctgggc tgtgtgcacg aaccccccgt tcagcccgac cgctgcgcct    3060
tatccggtaa ctatcgtctt gagtccaacc cggtaagaca cgacttatcg ccactggcag    3120
cagccactgg taacaggatt agcagagcga ggtatgtagg cggtgctaca gagttcttga    3180
agtggtggcc taactacggc tacactagaa gaacagtatt tggtatctgc gctctgctga    3240
agccagttac cttcggaaaa agagttggta gctcttgatc cggcaaacaa accaccgctg    3300
gtagcggtgg tttttttgtt tgcaagcagc agattacgcg cagaaaaaaa ggatctcaag    3360
aagatccttt gatcttttct acggggtctg acgctcagtg gaacgaaaac tcacgttaag    3420
ggattttggt catggctagt taattaacat ttaaatcagc ggccgcaata aaatatcttt    3480
attttcatta catctgtgtg ttggtttttt gtgtgaatcg taactaacat acgctctcca    3540 tcaaacaaa acgaaacaaa acaaactagc aaaataggct gtccccagtg caagtgcagg    3600
tgccagaaca tttctctatc gaa                                              3623
```

<210> SEQ ID NO 6
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Asn Ala Ser Leu Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Leu Arg Ser Pro
                85                  90                  95

Ile Thr Phe Gly Gln Gly Thr Lys Val Glu Ile Lys Arg
            100                 105

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5